United States Patent [19]

Brown-Skrobot

[11] Patent Number: 5,641,503
[45] Date of Patent: *Jun. 24, 1997

[54] ADDITIVES TO TAMPONS

[75] Inventor: Susan Kay Brown-Skrobot, Hamilton Square, N.J.

[73] Assignee: McNeil-PPC, Inc., Skillman, N.J.

[*] Notice: The term of this patent shall not extend beyond the expiration date of Pat. No. 5,389,374.

[21] Appl. No.: 374,386

[22] Filed: Jan. 13, 1995

Related U.S. Application Data

[63] Continuation of Ser. No. 183,446, Jan. 14, 1994, abandoned, which is a continuation of Ser. No. 41,134, Mar. 29, 1993, abandoned, which is a continuation of Ser. No. 864,704, Apr. 7, 1992, abandoned, which is a continuation of Ser. No. 695,358, May 3, 1991, abandoned, which is a continuation of Ser. No. 508,521, Apr. 17, 1990, abandoned, which is a continuation of Ser. No. 343,965, Apr. 27, 1989, abandoned.

[51] Int. Cl.$^6$ ................................................ A61F 13/02
[52] U.S. Cl. .................... 424/431; 424/404; 424/411; 424/446; 604/360; 604/904
[58] Field of Search .................... 424/431, 404, 424/411, 446; 604/360, 904

[56] References Cited

U.S. PATENT DOCUMENTS

| | | | |
|---|---|---|---|
| 3,052,607 | 9/1962 | Hirsh | 167/82 |
| 3,219,525 | 11/1965 | Berkow et al. | 167/58 |
| 3,584,119 | 6/1971 | Langley | 424/148 |
| 3,970,759 | 7/1976 | Frankenfeld et al. | 424/343 |
| 4,022,775 | 5/1977 | Kabara | 426/532 |
| 4,067,997 | 1/1978 | Kabara | 424/312 |
| 4,113,851 | 9/1978 | Leveen et al. | 424/28 |
| 4,347,237 | 8/1982 | Evenstad et al. | 424/78 |
| 4,374,522 | 2/1983 | Olevsky | 128/285 |
| 4,393,871 | 7/1983 | Vorhauer et al. | 609/58 |
| 4,405,323 | 9/1983 | Auerbach | 604/285 |
| 4,413,986 | 11/1983 | Jacobs | 604/14 |
| 4,431,427 | 2/1984 | Lefren et al. | 604/285 |
| 4,485,029 | 11/1984 | Kato et al. | 252/106 |
| 4,551,148 | 11/1985 | Riley et al. | 604/890 |
| 4,582,717 | 4/1986 | von Bittera et al. | 427/2 |
| 4,585,792 | 4/1986 | Jacob et al. | 514/474 |
| 4,722,936 | 2/1988 | Jacob | 514/474 |
| 4,722,937 | 2/1988 | Jacob et al. | 514/474 |
| 4,769,021 | 9/1988 | Kass | 604/367 |
| 4,788,060 | 11/1988 | Endicott et al. | 424/443 |
| 4,788,180 | 11/1988 | Bloch | 514/26 |
| 4,921,694 | 5/1990 | Hoppe et al. | 424/65 |
| 4,981,686 | 1/1991 | Hardy | 424/93 |
| 4,997,851 | 3/1991 | Isaacs et al. | 514/558 |
| 5,000,749 | 3/1991 | Le Veen et al. | 604/904 |

FOREIGN PATENT DOCUMENTS

| | | |
|---|---|---|
| 1123155 | 5/1982 | Canada . |
| 1192701 | 9/1985 | Canada . |
| 0117613 | 9/1984 | European Pat. Off. . |
| 0297310 | 1/1989 | European Pat. Off. . |
| 0302836 | 2/1989 | European Pat. Off. . |
| 522M | 5/1961 | France . |

(List continued on next page.)

OTHER PUBLICATIONS

Material Safety Data Sheet for Leomin H5G-R, 1988.

Altenbern, *Protease Inhibitors Suppress Enterotoxin B formation by Staphylococcus Aureus*, FEMS Microbiology Letters 3 (1978) pp. 199–202.

(List continued on next page.)

*Primary Examiner*—D. Gabrielle Phelan

[57] ABSTRACT

Absorbent products, especially catamenial tampons, for absorbing body fluids, such as menstrual fluid, blood and wound exudates, comprise an amount of a compound effective to inhibit the production of toxic shock syndrome toxin-1 by Staphylococcus aureus bacteria when the products are brought into contact with the bacteria. The compound is selected from the group consisting of monoesters of a polyhydric aliphatic alcohol and a $C_8$–$C_{18}$ fatty acid; diesters of a polyhydric aliphatic alcohol and a $C_8$–$C_{18}$ fatty acid; and mixtures thereof. The monoesters and diesters have at least one hydroxyl group associated with their aliphatic alcohol residue.

8 Claims, 7 Drawing Sheets

GROWTH OF Mn8

* DENOTES ADDITION OF 10 μg / ml OF GML
A, B, C, DENOTE TIME POINTS FOR SAMPLING

FOREIGN PATENT DOCUMENTS

| | | |
|---|---|---|
| 1307930 | 8/1962 | France . |
| 3309530C1 | 10/1984 | Germany . |
| 115016 | 2/1957 | New Zealand . |
| 183977 | 4/1979 | New Zealand . |
| 191703 | 12/1981 | New Zealand . |
| 194821 | 12/1982 | New Zealand . |
| 198139 | 7/1985 | New Zealand . |
| 209843 | 3/1987 | New Zealand . |
| 210484 | 5/1988 | New Zealand . |
| 222761 | 10/1989 | New Zealand . |
| 219973 | 5/1990 | New Zealand . |
| 221168 | 8/1990 | New Zealand . |
| 1374105 | 11/1974 | United Kingdom . |
| 2107192 | 4/1983 | United Kingdom . |
| 86/05388 | 9/1986 | WIPO . |

OTHER PUBLICATIONS

Ansari et al., *Sodium Bicarbonate Sodium Bicarbonate Douching for Improvement of the Postcoital Test*, Fertility and Sterility, vol. 33, No. 6, (Jun. 1980) pp. 608–612.

Flournoy et al., *The Role of Lauricidin as an Antimicrobial Agent*, Drugs of Today, vol. 21, No. 8, (1985) pp. 373–377.

Gossel, *Feminine Hygiene Products: Why Your Advice is Needed*, U.S. Pharmacist, (May 1986), pp. 20–27.

Iandolo. *Genetic Analysis of Extravellular Toxins of Staphylococcus Aureus*, Annu. Rev. Microbiol. (1989) 43: pp. 375–402.

Iandolo et al., *Regulation of Staphylococcal Enterotoxin $B^1$*, Infection and Immunity, vol. 16, No. 2, (May, 1977), pp. 610–616.

Ibrahim et al., *Inhibition of Growth of Staphylococcus aureus and Enterotoxin–A Production in Cheddar Cheese Prod. with Induced Starter Failure*, J. of Food Protec. vol. 44, No. 3, (Mar. 1981) pp. 189–193.

Kabara, *Structure–function Relationships of Surfactants as Antimicrobial Agents*, J. Soc. Cosmet. Chem., vol. 29, (Nov. 1978), pp. 733–741.

Notermans et al., *Effect of Glyceryl Monolaurate on Toxin Production by Clostridium Botulinum in Meat Slurry*, J. of Food Safety vol. 3, (1981), pp. 83–88.

Orden et al., *Detect. of Staph. Enterotoxin and Toxic Shock Synd. Toxin–1 (TSST–1) by (1991), Immunoblot Comb. with a Semiautomated Electrophoresis System*, J. of Immuno. Meth. V. 144, pp. 197–202.

Reiser et al., *Prod. of Toxic Shock Synd. Toxin 1 by Staph. aureus Restricted to Endogenous Air in Tampons*, J. of Cl. Microb., vol. 25, No. 8, (Aug. 1987), pp. 1450–1452.

Robbins et al., *Produc. of Toxic Shock Synd. Toxin 1 by Staphy. aureus as Determined by Tampon Disk–Membrane–Agar Method*, J. of Clin. Microbio., V. 25, No. 8, (Aug. 1987), pp. 1446–1449.

Schlivert, *Staphy. Enterotoxi B and Toxic–Shock Synd. Toxin–1 are Significantly Assoc. With Non–Menstrual TSS*, The Lancet, May 17, 1986, vol. 1, pp. 1149–1150, (Abstract).

Schlivert et al., *Toxic Shock Synd. Staphylococcus Aureus: Effect of Tampons on Toxic Shock Synd. Toxin Production*, Obstetrics & Glynecology, vol. 64, No. 5 (Nov. 1984), pp. 666–671.

Smith et al., *Enterotoxin A Synthesis in Staphylococcus aureus: Inhibition by Glycerol and Maltose*, J. of Gen. Microbiology, (1985), 132, pp. 3375–3380.

Smith et al., *Effect of Glucose Analogs on the Synthesis of Staphylococcal Enterotoxin A*, Journal of Food Safety 8, (1987), pp. 139–146.

Strobino et al., *Exposure to Contraceptive Creams, jellies and Douches and their Effect on the Zygote*, Society for Epidemiologic Research: Abstracts, pp. 434.

Tierno et al., *In vitro Amplification of Toxic Shock Syndrome Toxin–1 by Intravaginal Devices*, Contraception, vol. 31, No. 2 (Feb. 1985), pp. 185–194.

Garbe, et al., *Staphy. aureus Isolates from Patients with Nonmenstrual Toxic Shock Synd.*, JAMA, May 3, 1985, 253 (17) pp. 2538–2542.

Humphreys, et al., *Enterotoxin Production by Staphy. aureus Isolates from Cases of Septicaemia and from Healthy Carriers*, J. Med. Microbiology, Mar. 1989, 28, (3) pp. 163–172.

Crass, et al., *Involvement of Staphy. Enterotoxins in Nonmenstrual Toxic Shock Synd.*, J. Clin. Microbiol., Jun. 1986, 23, (6), pp. 1138–1139.

Northern Blot
tsf gene probe

STRAIN RN5885 WAS GROWN IN BHI WITH 0.20 μg/ml OF GML. AT THE INDICATED THE CELLS WERE ANALYZED FOR β-LACTAMASE ACTIVITY.

STRAIN RN5885 WAS GROWN IN BHI WITH 0.20 μg/ml OF GML. AT THE INDICATED THE CELLS WERE ANALYZED FOR β-LACTAMASE ACTIVITY.

GROWTH OF RN7220 7/24/91

AFFECT OF GML ON ALPHA HEMOLYSIN PRODUCTION

GROWTH OF RN8052 AND RN8053 9/9/91 pH IS DRIVING blaz IN agr+ AND agr- STRAINS 9/9/91

ADDITIVES TO TAMPONS

This is a continuation of application Ser. No. 08/183,446, filed Jan. 14, 1994, now abandoned, which is a Continuation of Ser. No. 08/041,134,filed Mar. 29, 1993, now abandoned, which is a Continuation of Ser. No. 07/864,704, filed Apr. 7, 1992, now abandoned, which is a Continuation of Ser. No. 07/695,358, filed May 3, 1991, now abandoned, which is a Continuation of Ser. No. 07/508,521, filed Apr. 17, 1990, now abandoned, which is a Continuation of Ser. No. 07/343,965, filed Apr. 27, 1989, now abandoned.

FIELD OF THE INVENTION

The present invention relates to absorbent products and especially to absorbent products such as tampons, sanitary napkins, wound dressings and the like which are adapted to absorb body fluids like menstrual fluid, blood and wound exudates. More particularly, the invention relates to catamenial tampons which, owing to the presence therein or thereon of certain inhibitory agents, reduce the amount of toxins produced by bacteria coming into contact therewith.

BACKGROUND OF THE INVENTION

Menstrually occurring toxic shock syndrome (TSS), a severe and sometimes fatal multi-system disease associated with infection or colonization by Staphylococcus aureus (S. aureus) bacteria, has been linked to the use of tampons during menstruation. The disease is believed to be caused by toxic shock syndrome toxin-1 (TSST-1), the toxin produced by the majority of Staphlococcal strains isolated from menstrual TSS patients.

Subsequent to the publication of reports associating toxic shock syndrome with the use of tampons, a number of investigators undertook studies designed to evaluate the effect of tampons on growth of S. aureus bacteria as well as the effect of tampons on the production of TSST-1 by that bacteria. Early efforts to elucidate the role of tampons in TSS yielded conflicting data. Schlievert et al. (Obstet. Gynecol., Vol. 64, pp. 666–670, November 1984) studied the effect of tampons on S. aureus to evaluate whether or not tampon components increase growth of S. aureus and production of toxic shock syndrome toxin-1. It was concluded that, under the test conditions of their study, tampon components provide neither nutrients for growth of toxic shock syndrome S. aureus nor factors that induce production of toxic shock syndrome toxin-1 above control levels. After six hour incubation, some commercially available tampons which were tested were inhibitory to bacterial growth and suppressed toxin production. Others suppressed toxin production but did not inhibit cell growth. One tampon inhibited cell growth but increased the amount of toxin produced. On the other hand, Tierno and Hanna (Contraception, Vol. 31, pp 185–194, 1985) reported that in their experiments tampons did stimulate S. aureus to produce TSST-1.

Reiser et al. (J. Clin. Microbiol., Vol. 25, No. 8, pp 1450–1452, August 1987) thereafter reported the results of tests they conducted to determine the effect of four brands of tampons on production of toxic shock syndrome toxin-1. The amount of air available to the tampons which were tested was limited to that contained in sacs (made from cellulose sausage casing with a molecular weight cut-off of less than 10,000) in which the tampons were enclosed during testing. This method was deemed advantageous in that the limited amount of available air was thought to mimic more closely than previously used methods the in vivo condition in the vagina during menstruation with a tampon in place and in that the tampons which were tested were not altered prior to testing. The results of the tests conducted by Reiser et al. indicated that tampons provide increased surface area for the S. aureus bacteria to grow and adequate oxygen for toxin production. No significant inhibition of growth of the staphylococci bacteria or TSST-1 production by any of the tampons tested was noted.

Robbins et al., publishing in J. Clinical Microbiol., Vol. 25, No. 8, pp. 1446–1449, August 1987 at the same time as Reiser et al., reported the effect of 17 commercially available tampons on TSST-1 toxin production using a disk-membrane-agar (DMA) method, with incubation at 37° C. for 19 hours under 5% $CO_2$ in air. Filter membranes overlaying agar medium (with or without blood) in small petri dishes were spread inoculated with a TSST-1 producing strain of S. aureus. Robbins et al. concluded that the main role of tampons in TSS may be that of providing a fibrous surface for heavy colonization and sufficient air for TSST-1 production. In addition, they found evidence of inhibition of TSST-1 production by additives such as the deodorant/surfactant used in a commercially available deodorant tampon and a decrease in TSST-1 production by inhibiting growth of S. aureus as was observed in the case of a different commercially available tampon. It was thought that both inhibition of TSST-1 production and inhibition of S. aureus growth might prove to be important in reducing the risk of TSS.

U.S. Pat. No. 4,405,323 to Auerbach discloses a tampon designed to eliminate the hazards of toxic shock syndrome and dysmenorrhea. The tampon has incorporated therein an antibacterial agent which is said to disperse on contact with body fluids and prevent development of the organisms which produce the toxins which cause toxic shock syndrome. Among the antibacterial materials disclosed for use are povidone-iodine compound, mercury, zinc, penicillin, erythromycin and nitrofurazone.

Patent Cooperation Treaty Publication No. WO 86/05388 (published Sep. 25, 1986) to Kass teaches that the inclusion of a salt of a nontoxic divalent cation in absorptive pads, e.g. catamenial tampons, inhibits production of toxic shock syndrome toxin-1 and other staphylococcal products during use of said absorptive pad. Suitable salts include those of magnesium, barium, calcium or strontium (preferred) or of other divalent cations such as zinc, manganese, copper, iron, nickel and the like. The anionic portion of the salt is not critical. Magnesium stearate and magnesium acetate are particularly preferred salts for use in the invention.

In U.S. Pat. No. 4,374,522 to Olevsky it is stated that patterns of use of catamenial tampon seem to indicate that high absorptive capacity with the concomitant extended period of use of certain tampons are factors which contribute to the formation of toxic shock syndrome. The invention theorizes that tampons having limited absorptive capacity and requiring relatively more frequent changes may be desirable. The Olevsky patent provides a tampon made of conventional cellulosic materials, such as rayon fibers, which have been compressed into a bullet-shape with an open bottom surface sealed by a fluid impermeable sheet. The fluid impermeable bottom and the traditional bullet shaped pledger define a hollow core central reservoir area which is said to serve as a reservoir for excess menstrual fluid.

U.S. Pat. No. 4,431,427 to Lefren et al. discloses menstrual tampons comprising physiologically safe, water-soluble acids in their monomeric, oligomeric or polymeric forms. Citric, glycolic, malic, tartaric and lactic acids are disclosed as being useful in the practice of the invention. The presence of one or more of the above-noted acids in a tampon is said to inhibit the growth of bacteria responsible for toxic shock. Where an acid is used in its polymeric form, the tampon may additionally include an enzyme to hydrolyze the polymeric acid to its monomeric form.

Canadian Patent No. 1,123,155 to Sipos discloses a catamenial tampon for preventing toxic shock syndrome during menstrual flow. The body of the tampon, which is open at the insertion end and is closed at the withdrawal end, is snugly surrounded in its expanded condition by a fluid proof, thin and flexible membrane. This membrane, which can be made of polyethylene sheet, is biased against the vaginal wall during use of the tampon, is neutral to the vaginal mucosa and is completely impermeable to bacteria, viruses and toxic decomposition products of the menstrual flow.

Canadian Patent No. 1,192,701 to Bardhan discloses a tampon for the absorption of menstrual flow and comprising an inner layer of liquid-absorbent material and an outer layer which surrounds and encloses the inner layer. Menstrual discharge may flow inwardly to the inner layer but the outer layer is impervious to the passage of menstrual fluid outwardly from the inner layer. A plurality of liquid absorbent wicks extending from the inner layer through apertures formed in the outer layer serve as conduits for the flow of menstrual discharge from outside the tampon to the inner layer thereof. The disclosed structure is said to minimize the availability of discharge outside the tampon with a resulting reduction in the likelihood of growth of S. aureus and consequently its production of toxin. This patent also discloses that an antimicrobial compound which is bactericidal or bacteriostatic to S. aureus may be included in the inner layer. The antimicrobial agent may take the form of an antibiotic (such as penicillin, erythromycin, tetracycline or neomycin), a chemotherapeutic agent (such as a sulfonamide) or a disinfectant (such as phenol). The patent states that since the tampon is protected by its outer layer from contact with the vaginal wall, the risk of an allergic or other adverse reaction to the anti-microbial agent is minimized, and since the antimicrobial agent is also protected by the outer layer from contact with menstrual discharge, there is little risk of the destruction of commensal organisms in the vagina or development of resistance to the antimicrobial agent by S. aureus in any menstrual discharge outside the vagina.

S. Notermans et al. (Journal of Food Safety, Vol. 3 (1981), pages 83–88) reported that glyceryl monolaurate, when used in the proportion of 5 g per kg. of meat slurry (pH 6.0–6.2) inhibited toxin. productions by *Clostridium botulinum* type A, type B and type E. This article does not mention *Staphylococcus aureus* nor any toxin(s) produced therefrom nor does it mention absorbent products or toxic shock syndrome.

U.S. Pat. No. 4,585,792 to Jacob et al. discloses that L-ascorbic acid when topically applied to the vaginal area of a human female during manses will inactivate toxins known to contribute to Toxic Shock Syndrome. The ascorbic acid compound may be carried by a vaginal tampon. The disclosure of U.S. Pat. No. 4,722,937, is to the same effect.

U.S. Pat. No. 4,413,986 to Jacobs discloses a sterilely-packaged tampon assembly for sterile insertion of a tampon into the vagina and having a guide tube telescoped around an insertion tube and a flexible sheath attached to the inner end of the guide tube and tucked into the inner end of the insertion tube. In use, as the insertion tube is pushed through the guide tube and into the vagina, the flexible sheath is pulled over the inner end of the insertion tube and extends along the exterior thereof. The portion of the insertion tube which is inserted into the vagina is at all times fully sheathed by the flexible sheath.

SUMMARY OF THE INVENTION

In accordance with the present invention, it has now been discovered that an absorbent product comprising a compound selected from the group consisting of:

a) a monoester of a polyhydric aliphatic alcohol and a fatty acid containing from eight to eighteen carbon atoms and wherein said monoester has at least one hydroxyl group associated with its aliphatic alcohol residue;

b) diesters of a polyhydric aliphatic alcohol and a fatty acid containing from eight to eighteen carbon atoms and wherein said diester has at least one hydroxyl group associated with its aliphatic alcohol residue; and c) mixtures of the aforesaid monoesters and diesters unexpectedly reduces the amount of toxic shock syndrome toxin-1 produced in vitro when said absorbent product is exposed to *Staphylococcus aureus* bacteria.

The fatty acid portion of the aforementioned monoesters and diesters may be derived from caprylic, captic, lauric, myristic, palmitic and stearic acids, which are saturated fatty acids whose chain lengths, respectively, are $C_8$, $C_{10}$, $C_{12}$, $C_{14}$, $C_{16}$ and $C_{18}$. The fatty acid portion of the aforementioned monoesters and diesters may be derived as well from unsaturated fatty acids having carbon chain lengths also ranging from $C_8$ to $C_{18}$, one example of such unsaturated fatty acids being oleic acid. The preferred fatty acid for use in the practice of the present invention is lauric acid, a saturated fatty acid whose chemical formula is $C_{11}H_{23}COOH$.

As used in this specification and the appended claims, the term "aliphatic" has the meaning usually accorded it in organic chemistry, i.e. "aliphatic" refers to organic compounds characterized by straight—or branched—chain arrangement of the constituent carbon atoms.

As used in this specification and the appended claims, the term "polyhydric" refers to the presence in a chemical compound of at least two hydroxyl (OH) groups. Thus, a polyhydric aliphatic alcohol is one which has at least two hydroxyl groups and in which the carbon backbone is either straight or branched.

Polyhydric alcohols suitable for forming monoesters and/or diesters for use in the practice of the present invention are 1,2-ethanediol; 1,2,3-propanetriol (glycerol); 1,3-propanediol; 1,4-butanediol; 1,2,4-butanetriol and the like. The preferred polyhydric aliphatic alcohol for forming monoesters and diesters for use in the practice of the present invention is 1,2,3-propanetriol (commonly called glycerol) whose formula is $HOCH_2CH(OH)CH_2OH$.

It will be observed that the esters which are useful in the practice of the present invention have at least one hydroxyl group associated with their aliphatic alcohol residue. Thus, it will be understood that the monoester of 1,2-ethanediol and one of the aforementioned fatty acids may be used in the practice of the present invention because said ester, whose general formula is

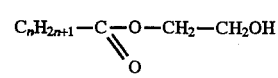

has at least one hydroxyl group (i.e. the hydroxyl group at the far right-hand side of the structural formula shown above) in that portion of the ester derived from the aliphatic alcohol 1,2-ethanediol. On the other hand, it will be understood that the diester of 1,2-ethanediol and one of the aforementioned fatty acids cannot be used in the practice of the present invention because said ester, whose general formula is

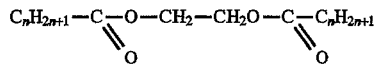

does not have at least one hydroxyl group in that portion of the ester derived from the 1,2-ethanediol.

The monoester of glycerol and one of the designated fatty acids may be used in the practice of the present invention because that ester will have two hydroxyl groups associated therewith which are derived from the glycerol. The diester of glycerol and one of the designated fatty acids may also be used because that ester will have one hydroxyl group associated therewith which is derived from the aliphatic alcohol glycerol. Indeed, as will be seen hereinafter, blends of glycerol monolaurate and glycerol dilaurate have been found to be useful in the practice of the present invention. Finally, it will be understood that the triester of glycerol and one of the designated fatty acids cannot be used in the practice of the present invention because that ester does not have at least one hydroxyl group in that portion thereof which is derived from the aliphatic alcohol, i.e. glycerol.

Preferred esters for use in the practice of the present invention are glyceryl monolaurate, glyceryl dilaurate and mixtures thereof.

In accordance with the invention, the absorbent product contains an amount of the above-described ester which is effective to inhibit the formation of TSS toxin-1 when said product is exposed to *S. aureus*. For example, effective amounts have been found to be from about 0.1% and higher and, preferably, at least about 0.5% of the specified mono- or diester compound (or mixtures thereof), based on the weight of the absorbent material comprising the absorbent product. As used herein, the term "absorbent material" includes natural or synthetic fibers, films, foams, wood pulp, peat moss, superabsorbent polymers and the like which are capable, either inherently or by virtue of the manner in which they have been assembled, of absorbing liquids such as water, urine, menstrual fluids, blood, wound exudates and the like.

GENERAL PROCEDURE FOR PREPARING TAMPONS OF THE INVENTION

Figure 1:
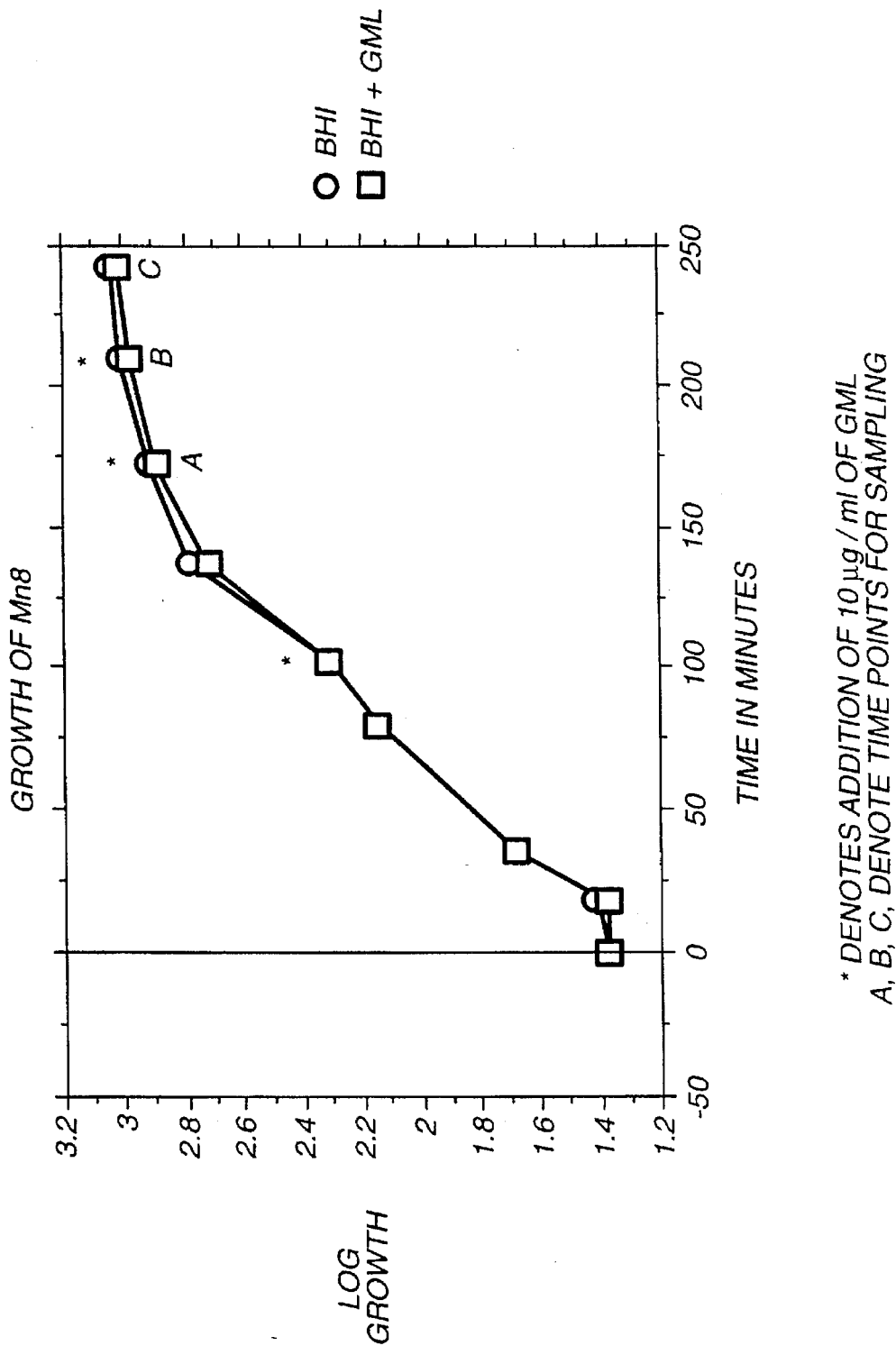
FIG. 1 illustrates the growth curves of cultures with and without one of the toxin-inhibiting compounds of the present invention.

During the course of conducting the investigations forming the basis for the present patent application, varying amounts of the aforementioned ester compounds (or mixtures thereof) were added to several different kinds of tampons. These tampons included ones prepared in the laboratories of the assignee of the present patent application as well as commercially available tampons made by several different manufacturers. Tampons of one manufacturer had different weights from those of another manufacturer and, indeed, no two tampons from a given manufacturer had identical weights. The ester compounds to be investigated were dissolved in isopropyl alcohol to form solutions which were then uniformly applied, by pipetting, to the outer surfaces of the various tampons, after which the isopropyl alcohol was evaporated to provide a tampon comprising the ester compound.

In order to ensure that the absorptive capacity of the tampons was not exceeded, it was decided to fix the amount of isopropyl alcohol solution applied to each tampon at four (4) grams in all cases. In view of this desire to hold constant the weight of isopropyl alcohol solution applied to each tampon, it was necessary to vary the concentration of ester compound in the isopropyl alcohol solution in order to vary the level of the selected ester compounds in the tampon. Accordingly, the following general procedure was used to apply a given ester material to a tampon.

Tampons were labeled for identification and weighed to the nearest one-tenth of a gram. The amount of ester required to give the desired concentration in the treated tampon was then calculated. Solutions of the ester in reagent grade isopropyl alcohol were prepared at concentrations such that four (4) grams of the solution contained the amount of ester to be included in the tampon to be tested. In this manner, the amount of ester in a given tampon could be varied while the total weight of the ester/isopropyl alcohol solution used to prepare each individual tampon was held constant at four (4) grams. For example, if the untreated tampon weighed 2.6 grams, then 0.26 gram of ester was required to provide a tampon comprising 10% of the ester based on the weight of the untreated tampon (i.e. 2.6 gram tampon weight×0.10= 0.26 gram ester). In this instance, six and one-half (6.5) grams of ester were dissolved in ninety-three and one-half (93.5) grams of reagent grade isopropyl alcohol to give a solution containing six and one-half (6.5%) by weight of ester. Four (4) grams of this solution contained the required 0.26 gram of ester. As another example, if the untreated tampon weighed 2.8 grams, and it was desired that the concentration of ester be one percent (1%) based on the weight of the untreated tampon, a solution containing 0.70 grams of ester and 99.3 grams of isopropyl alcohol was prepared. Four grams of this solution then contained the required 0.028 grams of ester.

As a third example, if the untreated tampon weighed 2.5 grams, and it was desired that the concentration of ester be 0.1% based on the weight of the untreated tampon, a solution containing 0.0625% by weight of ester in isopropyl alcohol was prepared. Four (4) grams of this solution contained the required 0.0025 gram of ester.

All solutions of ester compound in isopropyl alcohol were thoroughly stirred to ensure uniformity. In addition, especially at higher concentrations, the rate of dissolution of the ester could be increased by warming the ingredients to about 60° C., e.g. in a heated water bath.

Once the tampon had been weighed and the appropriate solution of ester in reagent grade isopropyl alcohol had been prepared in the manner explained above, four (4) grams of the ester/isopropyl alcohol solution (at room temperature) were uniformly applied, by pipetting, to the outer surfaces of the tampon. Tampons were rotated during the application of the ester solution to ensure as uniform an application as possible. The isopropyl alcohol was then evaporated at 70° C. in a hooded drying oven to yield a tampon comprising the desired level of ester compound.

The foregoing procedure was used to prepare all the ester-containing tampons mentioned in the Examples of the present patent application.

DESCRIPTION OF THE PREFERRED EMBODIMENTS

In Example 1 which follows herein, the invention will be described in detail in connection with a catamenial tampon comprising an absorbent material, a liquid-pervious covering fabric, and an amount of a mixture of glycerol monolaurate and glycerol dilaurate which is effective to inhibit the production of toxic shock syndrome toxin-1 by *S. aureus* bacteria when said bacteria are brought into contact with the tampon. It will be understood that the principles of the invention apply as well to other absorbent products such as wound dressings, disposable diapers, sanitary napkins and other kinds of tampons, such as those intended for medical, surgical, dental and/or nasal use.

Catamenial tampons comprising rayon fibers as their absorbent material were prepared as follows. The rayon fibers employed were 3-denier, vicose rayon staple fibers having a length of 1⅛ inches (2.86 cm) and 11–25 crimps per inch (about 4.3–9.8 crimps per centimeter). The fibers were 100% vicose rayon, i.e. they were substantially free of all finishes and additives, such as surfactants and the like, commonly used in commercial production.

Using commercially available carding equipment, the above-described rayon fibers were carded into a fibrous web weighing about 520 grains/yd$^2$ (33.6 grams/meter$^2$). The carded web of rayon fibers was gathered into a tubular ribbon having a diameter of about one-inch (2.54 cm). This tubular ribbon was thereafter covered in a nonwoven fabric made from heat-fusible fibers and weighing about 0.25 oz/yd$^2$ (7.08 gm/m$^2$). The edges of the heat-fusible nonwoven fabric were overlapped slightly and subsequently heat treated to form a seal. The covered ribbon of rayon fibers was cut into blanks. A white rayon string was pierced and looped through each blank. The blank was then compressed in known fashion to provide a test tampon having a diameter of 0.47 inch (1.2 cm), a length of 1.75 inches (4.44 cm), and a weight of about 2.6 grams. The dangling portion of the withdrawal string was cut from the tampon prior to testing.

A mixture of glycerol monolaurate and glycerol dilaurate, commercially available under the tradename "Lauricidin", was obtained from Lauricidin, Inc. located in East Lansing, Mich., U.S.A. This mixture, which is hereinafter sometimes referred to as "Lauricidin", was analyzed and found to contain 93 percent by weight of glycerol monolaurate and 3.5 percent by weight of glycerol dilaurate. It is known that Lauricidin has antimicrobial properties and is non-toxic to humans. It has been suggested for use in anti-caries products, insecticides, cosmetic preparations and food compositions.

EXAMPLE 1

Tampons comprising, respectively, 0.1%, 1.0% and 10% by weight of the aforementioned Lauricidin mixture based on the weight of the untreated tampon were prepared using the above-mentioned test tampons. The Lauricidin mixture was applied to the test tampons according to the General Procedure for Preparing Tampons of the Invention described earlier in this application. The Lauricidin containing tampons were prepared in duplicate. The Lauricidin treated tampons were then tested according to the Tampon Sac Method reported by Reiser et al. in the Journal of Clinical Microbiology, Vol. 25, August 1987, pp. 1450–1452, the disclosure of which is hereby incorporated by reference. *Staphylococcus aureus* strain FRI-1169, obtained in lyophilized form from Dr. Merlin Bergdoll, Food Research Institute, University of Wisconsin, in Madison, Wisc., U.S.A., was employed in the tests. A *S. aureus* suspension was prepared by thoroughly mixing one (1) milligram of the lyophilized *S. aureus* strain to one (1) milliliter of Brain Heart Infusion (BHI) Broth (obtained from Difco Laboratories, Detroit, Mich., U.S.A.), transferring said mixture into a test tube containing five (5) milliliters of BHI Broth, thoroughly mixing again, and incubating for twenty-four (24) hours at 37° C. prior to use.

100 milliliters of brain heart infusion (BHI) agar (also obtained from Difco Laboratories in Detroit, Mich., U.S.A.) were put into each of ten 3.8 cm×20 cm culture tubes. Cellulose sacs were made and sterilized in the manner reported by Reiser et al. The sterile cellulose sacs were inoculated with the aforementioned *S. aureus* suspension in an amount sufficient to provide at the beginning of the test a concentration therein of 1×10$^8$ CFU/ml *Staphylococcus aureus* bacteria.

Each Lauricidin treated tampon to be tested was inserted into a sterile cellulose sac containing the *S. aureus* bacteria and each sac was then inserted into a culture tube containing the BHI agar. Two controls, each in duplicate, were used. In one control (called the "inoculum control"), an inoculated sac (with no tampon therein) was placed in each of two culture tubes containing BHI agar. In the second control, two untreated tampons (i.e. tampons made in the described manner but with no Lauricidin in the isopropyl alcohol) were placed in cellulose sacs which in turn were placed in culture tubes containing BHI agar. Thus, ten culture tubes were used in this test, four containing the aforementioned controls (two with tampons; two without tampons) and the others containing the aforementioned Lauricidin-treated test tampons in duplicate.

The concentrations of *S. aureus* strain FRI-1169 and toxic shock syndrome toxin-1 at the outset of the test (0 hours) and after incubation for 24 hours at 37° C. are shown in Table 1.

TABLE 1

THE EFFECT OF LAURICIDIN TREATED TAMPONS ON TSST-1 FORMATION
BY AND GROWTH OF *STAPHYLOCOCCUS AUREUS*

| SAMPLE | INITIAL CONCENTRATION OF *S. AUREUS* CELLS (CFU/ml) ($10^8$) | INITIAL CONCENTRATION OF TSST-1[a] (ng/ml) | FINAL CONCENTRATION OF *S. AUREUS* CELLS (CFU/ml) ($10^8$) | FINAL CONCENTRATION OF S. AUREUS CELLS[b] (/ml) | FINAL CONCENTRATION OF TSST-1[a] ug/ml |
|---|---|---|---|---|---|
| No tampon (control) | 1.0 | ND | 100 | 10.0 | 50 |
| Untreated Tampon (control) | 1.0 | ND | 100 | 10.0 | 31 |
| Tampon w/0.1% Lauricidin | 1.0 | ND | 794 | 10.9 | 15 |
| Tampon w/1.0% Lauricidin | 1.0 | ND | 158 | 10.2 | 0.09 |
| Tampon w/10.0% Lauricidin | 1.0 | ND | 316 | 10.5 | 0.08 |

ND = NOT DETECTED. Detection limit of the ELISA method of Reiser et al is 0.5 ng/ml.
[a] = As determined by the ELISA method reported by Reiser et al. in Applied and Environmental Microbiology, December 1982, pp. 1349–1355, the disclosure of which is hereby incorporated by reference.
[b] = Expressed as log to base 10.
All data above are mean determinations of duplicate samples.

The data in Table 1 show that *S. aureus* bacteria in the presence of a tampon comprising 0.1% (w/w) Lauricidin produce 51% less toxic shock syndrome toxin-1 (TSST-1) than when exposed to a control tampon containing no Lauricidin, in spite of the fact that there was no reduction in the actual number of viable *S. aureus* cells in the presence of the Lauricidin-treated tampon. The data further show that *S. aureus* bacteria in the presence of tampons comprising 1.0% (w/w) and 10.0% (w/w) of Lauricidin produced 99% less TSST-1 than did the same number of *S. aureus* cells in the presence of a control tampon containing no Lauricidin, again in spite of the fact that there was no reduction in the number of viable *S. aureus* cells in the presence of Lauricidin-containing tampons. The data show that although the number of viable *S. aureus* cells does not decrease when the cells are exposed to tampons containing various levels of Lauricidin, the actual amount of TSST-1 produced by those cells is significantly reduced (as in the case of the tampon treated with 0.1% Lauricidin) or substantially eliminated (as in the case of tampons treated with 1.0% and 10% of Lauricidin). In other words, while Lauricidin does not significantly reduce the number of viable *S. aureus* bacteria cells, but it does significantly inhibit the production of toxic shock syndrome toxin-1 by those cells.

Thus, it is believed that in vivo use of Lauricidin treated tampons in menstruating women would be beneficial in that the production of TSST-1 by any *S. aureus* bacteria normally present in the vagina would be significantly reduced. In addition, in preliminary studies conducted using the predominant microorganism present in the vagina, i.e. *Lactobacillus acidophilus,* it was found that said microorganism was not adversely affected when brought into contact with an Example 1 tampon comprising 1.0% (w/w) Lauricidin.

EXAMPLE 2

A second experiment was conducted to evaluate growth of, and TSST-1 production by, *S. aureus* cells in the presence of commercially available tampons treated with varying amounts of Lauricidin. Tampax* brand menstrual tampons (regular size, Lot No. 8L015Z) which had been purchased on the open market were employed in the experiment of this Example 2. These tampons were manufactured by Tambrands, Inc., Lake Success, N.Y., U.S.A. The Tampax* tampons comprised a cotton absorbent core, a rayon fabric covering, and a withdrawal string. The tampon withdrawal strings were cut from the tampons prior to testing. Tampons comprising 0.1%, 1.0% and 10% Lauricidin based on the weight of the untreated tampons were prepared in duplicate according to the aforementioned General Procedure. Two Tampax* tampons (with strings cut off), treated with isopropyl alcohol containing no Lauricidin and thereafter dried, were used as a control. The dried, Lauricidin-treated tampons and the control tampons, were then tested according to the procedure and conditions reported in Example 1. The test results are reported in Table 2.

TABLE 2

| THE EFFECT OF LAURICIDIN TREATED TAMPAX TAMPONS (LOT NO. 8L015Z) ON TSST-1 FORMATION BY *STAPHYLOCOCCUS AUREUS* (FRI-1169) | | | |
|---|---|---|---|
| SAMPLE | FINAL CONCENTRATION OF *S. AUREUS* CELLS (CFU/ml) ($10^8$) | FINAL CONCENTRATION OF *S. AUREUS* CELLS[b)] (/ml) | FINAL CONCENTRATION OF TSST-1[a)] (μg/ml) |
| 0% Lauricidin Tampon (control) | 5,248 | 11.72 | 27.50 |
| 0.1% Lauricidin On Tampon | 199 | 10.30 | 3.70 |
| 1.0% Lauricidin On Tampon | 251 | 10.40 | 1.05 |
| 10.0% Lauricidin On Tampon | 2.13 | 8.33 | 0.19 | a)= As determined by ELISA method (Reiser et al.).
b)= Expressed as log to base 10.
All sample determinations were made after 24 hrs. incubation at 37° C.
All data above are mean determinations of duplicate samples.

The data in Table 2 show that *S. aureus* bacteria in the presence of Tampax* brand tampons treated with varying amounts of Lauricidin produce less TSST-1 than when exposed to the control tampon containing no Lauricidin, the extent of the reduction in toxin production being related to the amount of Lauricidin in the tampons. Tampax* tampons treated with 0.1% by weight of Lauricidin resulted in an 86% reduction in TSST-1 produced compared to the control, while the Tampax* tampons treated with 1% and 10% by weight of Lauricidin resulted in, respectively, a 96% and 99% reduction. The results with the Tampax* brand tampons also show a reduction in the total number of S. aureus cells; this effect is dependent upon the concentration of Lauricidin in the tampon. At the end of the 24 hour incubation period, the log concentration of S. aureus cells in the presence of the control tampon was 11.72; the log concentration of S. aureus cells in the presence of the tampon containing 0.1% Lauricidin was 10.30 (12% less); the log concentration of S. aureus cells in the presence of the tampon containing 1.0% Lauricidin was 10.40 (11% less); and the log concentration of S. aureus cells in the presence of the tampon containing 10% Lauricidin was 8.33 (29% less).

EXAMPLE 3

A third experiment was conducted to evaluate growth of, and TSST-1 production by, S. aureus cells in the presence of commercially available tampons treated with varying amounts of Lauricidin. Playtex* brand menstrual tampons (regular size, Lot No. 3496P) which had been purchased on the open market were employed in the experiment of this Example 3. These tampons were manufactured by International Playtex Inc., Dover, Del., U.S.A. The Playtex* tampons were made of all rayon fiber and had a withdrawal string but no cover fabric. The tampon withdrawal strings were cut from the tampons prior to testing. Treated tampons comprising 0.1%, 1.0% and 10% Lauricidin based on the weight of the untreated tampon were prepared in duplicate according to the aforementioned General Procedure. Two Playtex* tampons (with strings cut off) without any Lauricidin treatment were used as a control. The dried Lauricidin-treated tampons and the untreated controls were then tested according to the procedure and conditions described in Example 1. The test results are reported in Table 3.

TABLE 3

THE EFFECT OF LAURICIDIN TREATED PLAYTEX TAMPONS (LOT NO. 3496P) ON TSST-1 FORMATION BY STAPHYLOCOCCUS AUREUS (FRI-1169)

| SAMPLE | FINAL CONCEN- TRATION OF S. AUREUS CELLS (CFU/ml) ($10^8$) | FINAL CONCEN- TRATION OF S. AUREUS CELLS[b] (/ml) | FINAL CONCEN- TRATION OF TSST-1[a] (μg/ml) |
|---|---|---|---|
| 0% Lauricidin Tampon (control) | 3,388 | 11.53 | 10.86 |
| 0.1% Lauricidin On Tampon | 213 | 10.33 | 2.69 |
| 1.0% Lauricidin On Tampon | 131 | 10.12 | 0.38 |
| 10.0% Lauricidin On Tampon | 3.23 | 8.51 | 0.29 |

[a] = As determined by ELISA method (Reiser et al.).
[b] = Expressed as log to base 10.
All sample determinations were made after 24 hrs. incubation at 37° C.
All data above are mean determinations of duplicate samples.

The data reported in Table 3 show that the amount of TSST-1 produced by S. aureus bacteria in the presence of Playtex* tampons treated with 0.1%, 1.0% and 10.0% w/w Lauricidin was reduced 75%, 96% and 97%, respectively, when compared to the amount of TSST-1 produced in the presence of a control tampon containing no Lauricidin. On the other hand, compared to control values, the Playtex* tampons treated with 0.1%, 1.0% and 10.0% w/w of Lauricidin resulted in 10%, 12% and 26% fewer S. aureus cells at the end of the 24 hour incubation period.

EXAMPLE 4

A fourth experiment was conducted to evaluate growth of, and TSST-1 production by S. aureus cells in the presence of another brand of menstrual tampons treated with varying amounts of Lauricidin. Rely* brand menstrual tampons (regular size, Lot No. 2060LC01A) which had been purchased prior to September 1980 on the open market were employed in the experiment of this Example 4. These tampons were manufactured by Procter & Gamble, Cincinnati, Ohio, USA. The Rely* tampons comprised carboxymethyl cellulose dispersed in a polyester foam which was wrapped in a nonwoven fabric made of spunbonded polyester fibers. They had the usual withdrawal strings. The tampon withdrawal strings were cut from the tampons prior to testing. Treated tampons comprising 0.1%, 1.0% and 10% Lauricidin based on the weight of the untreated tampon were prepared in duplicate according to the aforementioned General Procedure. Two Rely* tampons (with their withdrawal strings cut off) without any Lauricidin treatment were used as a control. The dried Lauricidin-treated tampons and the untreated control tampons were then tested according to the procedure and conditions described in Example 1. The test results are reported in Table 4.

TABLE 4

THE EFFECT OF LAURICIDIN TREATED RELY TAMPONS (LOT NO. 2060LC01A) ON TSST-1 FORMATION BY STAPHYLOCOCCUS AUREUS (FRI-1169)

| SAMPLE | FINAL CONCEN- TRATION OF S. AUREUS CELLS (CFU/ml) ($10^8$) | FINAL CONCEN- TRATION OF S. AUREUS CELLS[b] (/ml) | FINAL CONCEN- TRATION OF TSST-1[a] (μg/ml) |
|---|---|---|---|
| 0% Lauricidin Tampon (control) | 12,303 | 12.09 | 64.32 |
| 0.1% Lauricidin On Tampon | 2,818 | 11.45 | 6.92 |
| 1.0% Lauricidin On Tampon | 1,995 | 11.30 | 1.54 |
| 10.0% Lauricidin On Tampon | 1,096 | 11.04 | 0.09 |

[a] = As determined by ELISA method (Reiser et al.).
[b] = Expressed as log to base 10.
All sample determinations were made after 24 hrs. incubation at 37° C.
All data above are mean determinations of duplicate samples.

The data reported in Table 4 show that the amount of TSST-1 produced by S. aureus bacteria in the presence of the Rely* tampons treated with 0.1%, 1.0% and 10.0% w/w Lauricidin was reduced by 89%, 97% and 99%, respectively, when compared to the amount of TSST-1 produced in the presence of a control tampon containing no Lauricidin. Whereas, at the end of the 24 hour incubation period, the total S. aureus cell concentration (expressed as log to the base 10) in the presence of the control tampon was 12.09, the total S. aureus cell concentration (expressed as log to the base 10) in the presence of the Rely* tampon treated with 0.1%, 1.0% and 10% Lauricidin was, respectively, 11.45 (5.3% less), 11.20 (7.4% less) and 11.04 (7.8% less).

EXAMPLE 5

A fifth experiment was conducted to evaluate growth of, and TSST-1 production by S. aureus cells in the presence of commercially available tampons treated with varying amounts of Lauricidin. O.b.* brand menstrual tampons (regular size, Lot No. 0694T) which had been purchased on the open market were employed in the experiment of this Example 5. These tampons were distributed by Personal Products Company, Milltown, N.J., U.S.A. The o.b.* tampons comprise a blend of rayon and cotton. They included a withdrawal string but did not have an outer cover sheet. The tampon withdrawal strings were cut from the tampons prior to testing. Treated tampons comprising 0.1%, 1.0% and 10% Lauricidin based on the weight of the untreated tampon were prepared in duplicate according to the General Procedure described earlier herein. Two o.b.* tampons (with strings cut off) without any Lauricidin treatment were used as a control. The dried Lauricidin-treated tampons and the untreated control tampons were then tested according to the procedure and conditions described in Example 1. The test results are reported in Table 5.

TABLE 5

THE EFFECT OF LAURICIDIN TREATED O.b.* TAMPONS (LOT NO. 0694T) ON TSST-1 FORMATION BY *STAPHYLOCOCCUS AUREUS* (FRI-1169)

| SAMPLE | FINAL CONCEN-TRATION OF *S. AUREUS* CELLS (CFU/ml) ($10^8$) | FINAL CONCEN-TRATION OF *S. AUREUS* CELLS[b] (/ml) | FINAL CONCEN-TRATION OF TSST-1[a] (µg/ml) |
|---|---|---|---|
| 0% Lauricidin Tampon (control) | 3,388 | 11.53 | 13.46 |
| 0.1% Lauricidin On Tampon | 158 | 10.20 | 3.26 |
| 1.0% Lauricidin On Tampon | 316 | 10.50 | 0.28 |
| 10.0% Lauricidin On Tampon | 95 | 9.98 | 0.19 |

[a]= As determined by ELISA method (Reiser et al.).
[b]= Expressed as log to base 10.
All sample determinations were made after 24 hrs. incubation at 37° C.
All data above are mean determinations of duplicate samples.

The data presented in Table 5 show that the amount of TSST-1 produced by S. aureus bacteria in the presence of o.b.* tampons comprising 0.1%, 1.0% and 10% by weight Lauricidin was reduced by 75%, 98% and 98%, respectively, when compared to the amount of TSST-1 produced in the presence of a control o.b.* tampon containing no Lauricidin. The total S. aureus cell concentration (expressed as log to the base 10) in the presence of the control tampon was 11.53. The total S. aureus concentration (expressed as log to the base 10) in the presence of the o.b.* tampon treated with 0.1%, 1.0% and 10% by weight of the Lauricidin was, respectively, 10.20 (11% less), 10.50 (8.9% less), and 9.98 (13% less).

EXAMPLE 6

A sixth experiment was conducted to evaluate growth of, and TSST-1 production by S. aureus cells in the presence of commercially available tampons treated with varying amounts of Lauricidin. Kotex* Security* brand menstrual tampons (regular size, Lot No. 5C0907C) which had been purchased on the open market were employed in the experiment of this Example 6. These tampons were marketed by Kimberly-Clark Corporation, Neenah, Wisc., U.S.A. They comprised a blend of 60% cotton and 40% rayon, had the usual withdrawal string, and were covered with a nonwoven fabric made of polypropylene fibers. The tampon withdrawal strings were cut from the tampons prior to testing. Treated tampons comprising 0.1%, 1.0% and 10% Lauricidin based on the weight of the untreated tampon were prepared in accordance with the above-described General Procedure. Two Kotex* Security* tampons (with strings cut off) without any Lauricidin treatment were used as controls. The dried Lauricidin-treated tampons and the untreated control tampons were then tested according to the procedure and conditions described in Example 1. The test results are reported in Table 6.

TABLE 6

THE EFFECT OF LAURICIDIN TREATED KOTEX SECURITY TAMPONS, LOT NO. 5C0907C ON TSST-1 FORMATION BY STAPHYLOCOCCUS AUREUS (FRI-1169)

| SAMPLE | FINAL CONCEN-TRATION OF *S. AUREUS* CELLS (CFU/ml) ($10^8$) | FINAL CONCEN-TRATION OF *S. AUREUS* CELLS[b] (/ml) | FINAL CONCEN-TRATION OF TSST-1[a] (µg/ml) |
|---|---|---|---|
| 0% Lauricidin Tampon (control) | 1,698 | 11.23 | 10.19 |
| 0.1% Lauricidin On Tampon | 194 | 10.29 | 4.90 |
| 1.0% Lauricidin On Tampon | 426 | 10.63 | 0.09 |
| 10.0% Lauricidin On Tampon | 426 | 10.63 | 0.05 |

[a]= As determined by ELISA method (Reiser et al.).
[b]= Expressed as log to base 10.
All sample determinations were made after 24 hrs. incubation at 37° C.
All data above are mean determinations of duplicate samples.

The data presented in Table 6 show that the amount of TSST-1 produced by S. aureus bacteria in the presence of Kotex* tampons comprising 0.1%, 1.0% and 10% by weight of Lauricidin was reduced by 52%, 99% and 99%, respectively, when compared to the amount of TSST-1 produced under the same experimental conditions in the presence of a control Kotex* tampon containing no Lauricidin. The total concentration of S. aureus cells (expressed as log to the base 10) in the presence of the Kotex* tampons containing 0.1%, 1.0% and 10% by weight of Lauricidin was, respectively, 10.29 (8.4% less), 10.63 (5.3% less) and 10.63 (5.3% less).

As can be seen from the preceding Examples 1–6, a variety of tampons, one of which was made by the inventors (Example 1), others of which were commercially available (Examples 2, 3, 5 and 6) and one of which had been commercially available but was subsequently withdrawn from commercial distribution (Example 4), have been treated with varying levels of Lauricidin, a commercially available mixture comprising 93% by weight glycerol monolaurate and 3.5% by weight glycerol dilaurate. The data reported in Tables 1–6 show that, depending on the levels of Lauricidin in the tampons, S. aureus bacteria produce significantly less TSST-1 or, in other words, are inhibited from producing significant amounts of TSST-1 when compared to the amounts of TSST-1 produced, under the same experimental conditions, by S. aureus bacteria in the presence of control tampons containing no Lauricidin.

EXAMPLE 7

Test tampons of the kind used in Example I were used in this Example 7. Test tampons comprising 0.1%, 0.5%, and 1.0% Lauricidin based on the weight of the untreated test tampons were prepared according to the General Procedure described earlier herein and were tested according to the Tampon Sac Method described in Example 1. In this Example 7, however, the tampon sacs were inoculated with different strains of S. aureus bacteria prior to the insertion therein of the Lauricidin treated tampons. The respective strains of S. aureus tested are identified in Table 7. The concentration of S. aureus at the outset of the experiment was $1 \times 10^8$ CFU/ml. TSST-1 producing S. aureus strain FRI-1169 utilized in this Example 7 was obtained from Merlin Bergdoll, Ph.D., Food Research Institute, University of Wisconsin, Madison, Wisc. U.S.A. TSST-1 producing S. aureus strain designated 1169W was obtained from Fred Quimby, V. M. D., Ph.D., Cornell Medical School, New York, N.Y., U.S.A. A third S. aureus strain (specifically a substrain of FRI-1169) was isolated from the parent strain and designated TSS Isolate. This TSS Isolate can be obtained in a lyophilized state from S. K. Brown-Skrobot, Ph.D., Personal Products Company, Milltown, N.J., U.S.A. A fourth TSST-1 producing S. aureus strain designated Mn8, was obtained from Patrick Schlievert, Ph.D., University of Minnesota, Minneapolis-St. Paul, Minn., U.S.A. A fifth TSST-1 producing S. aureus strain designated 1187 was obtained from Keith T. Holland, Ph.D., University of Leeds, Leeds, England. All of the S. aureus strains tested in this example can be obtained from the aforementioned individuals.

Suspensions of the various strains were prepared as described in Example 1 and used to inoculate the sacs prior to insertion of the tampons which were then tested according to the Tampon Sac Method described in Example 1. Duplicate test tampons without any Lauricidin were used as controls. The test results are reported in Table 7.

The results shown in Table 7 show a reduction in TSST-1 formation with increasing concentration of Lauricidin. This was noted in all five strains which were tested. It was concluded from the test results that the beneficial effects of Lauricidin observed in Examples 1–6 were not specific to any particular TSST-1 producing S. aureus strain.

TABLE 7

THE EFFECT OF LAURICIDIN TREATED TAMPONS ON GROWTH OF AND TSST-1 PRODUCTION BY VARIOUS STRAINS OF S. AUREUS

| TSST-1 PRODUCING STRAIN | CONCENTRATION OF LAURICIDIN[a] (%) | TOTAL AMOUNT TSST-1 PRODUCED[b] (µg) |
|---|---|---|
| 1169W (Quimby Strain) | NONE | 56.54 |
| | 0.1 | 17.54 |
| | 0.5 | 0.35 |
| | 1.0 | 0.07 |
| FRI-1169 (Bergdoll Strain) | NONE | 48.75 |
| | 0.1 | 5.06 |
| | 0.5 | 0.04 |
| | 1.0 | 0.03 |
| TSS Isolate (Substrain of FRI-1169) | NONE | 53.04 |
| | 0.1 | 5.25 |
| | 0.5 | 1.27 |
| | 1.0 | 0.48 |
| Mn8 (Schlievert Strain) | NONE | 66.30 |
| | 0.1 | 0.66 |
| | 0.5 | 0.12 |
| | 1.0 | 0.05 |
| 1187 (Holland Strain) | NONE | 46.80 |
| | 0.1 | 6.63 |
| | 0.5 | 0.92 |
| | 1.0 | 0.58 |

[a] = based on weight of untreated tampon.
[b] = Total TSST-1 per tampon after 24 hr. incubation at 37° C.
All samples were tested for total TSST-1 produced using the ELISA method (Reiser et al.).

EXAMPLE 8

In this Example 8, tampons comprising various fatty acid esters were tested to determine their effect on growth of and TSST-1 formation by S. aureus bacteria (FRI-1169). Test tampons of the kind used in Example 1 were used for this Example 8. All of the test tampons weighed 2.6 grams. 0.65 gram of each fatty acid ester to be tested was dissolved in 99.35 grams of reagent grade or ester mixture isopropyl alcohol. Four (4) grams of each fatty acid ester solution were applied to the outer surfaces of each of two test tampons to provide treated tampons comprising 1% by weight of the ester or ester mixture based on the weight of the untreated test tampon. The alcohol was removed by evaporation at 70° C., after which the treated tampons were tested according to the Tampon Sac Method described in Example 1. Following is a list of the fatty acid esters which were evaluated:

Tampon No. 1—A mixture of glyceryl monocaprylate and glyceryl caprate. Caprylic acid is a saturated fatty acid containing 8 carbon atoms. Captic acid is a saturated fatty acid containing 10 carbon atoms. The mixture contained about 38.3% by weight of the caprylate ester, about 36.9% by weight of the caprate ester and about 0.6% free glycerine. The remainder of this mixture contained minor amounts of di- and triesters of the two fatty acids.

Tampon No. 2—Glyceryl monolaurate of 90–95% purity and containing 0.2% free glycerine and minor amounts of the di- and triesters. Lauric acid is a saturated fatty acid containing 12 carbon atoms.

Tampon No. 3—Glyceryl monomyristate of 90–95% purity and containing about 0.2% free glycerine and minor amounts of the di- and triesters. Myristic acid is a saturated fatty acid containing 14 carbon atoms.

Tampon No. 4—Glyceryl monopalmitate of 90–95% purity and containing 0.2% free glycerine and minor amounts of the di- and triesters. Palmitic acid is a saturated fatty acid containing 16 carbon atoms.

Tampon No. 5—Glyceryl monostearate of 90–95% purity and containing 0.2% free glycerine and minor amounts of the di- and triesters. Stearic acid is a saturated fatty acid containing 18 carbon atoms.

Tampon No. 6—Glyceryl monooleate of 90–95% purity and containing 0.2% free glycerine and minor amounts of the di- and triesters. Oleic acid is an unsaturated fatty acid containing 18 carbon atoms and one double bond.

In this Example 8, two untreated tampons were used as controls.

The results of the tests are shown in Table 8. The data show that there was a marked reduction in the amount of TSST-1 produced by *S. aureus* strain FRI-1169 in the presence of the tampons treated with the various fatty acid esters when compared to the amount of TSST-1 produced in the presence of the untreated control tampons. The reduction in the amount of TSST-1 produced ranged from about 90% to 99%, except in the case of the tampon containing glyceryl monostearate. The 60% reduction in TSST-1 production observed in the case of the tampon containing glyceryl monostearate, though not as high as that obtained with the tampons containing other esters, was nevertheless quite substantial and is regarded as significant. No corresponding pattern of reduction in the number of viable *S. aureus* cells was observed. It should be noted, however, that at the end of the 24 hour incubation period, there were fewer viable *S. aureus* cells on the treated tampons than on the tampons having no ester treatment.

from Stepan Chemical Company, Maywood, N.J. U.S.A. under the tradename Kessco. This mixture was analyzed and found to contain 50% by weight of glyceryl monolaurate, and 37% by weight of glyceryl dilaurate. Another such mixture was obtained from Henkel Corporation under the name Monomuls 90-L12 and found to contain 96% by weight of glyceryl monolaurate. No glyceryl dilaurate was detected. Using the aforementioned General Procedure and the same test tampons as those used in Example 1, the following tampons were prepared in duplicate:

Tampons comprising, respectively, 0.1%, 0.5% and 1.0% of Lauricidin based on the weight of the untreated test tampons;

Tampons comprising, respectively, 0.1%, 0.5% and 1.0% of the Kessco ester mixture based on the weight of the untreated test tampons; and

TABLE 8

IMPACT OF VARIOUS GLYCERYL ESTER COMPOUNDS ON GROWTH OF AND TSST-1 FORMATION BY *STAPHYLOCOCCUS AUREUS* (FRI-1169)

| SAMPLE | FINAL CONCENTRATION OF S. AUREUS CELLS (CFU/ml) | FINAL CONCENTRATION OF S. AUREUS CELLS[b] (/ml) | TOTAL AMOUNT TSST-1 PRODUCED[a] (ug) | REDUCTION IN TSST-1 FORMATION (%) |
|---|---|---|---|---|
| Control Tampon | $4.20 \times 10^9$ | 9.62 | 17.15 | — |
| Tampon No. 1 | $5.80 \times 10^6$ | 6.76 | 0.18 | 98.9 |
| Tampon No. 2 | $6.56 \times 10^6$ | 6.81 | 0.14 | 99.1 |
| Tampon No. 3 | $5.04 \times 10^8$ | 8.83 | 0.58 | 96.5 |
| Tampon No. 4 | $1.44 \times 10^9$ | 9.15 | 1.75 | 89.7 |
| Tampon No. 5 | $6.08 \times 10^8$ | 8.78 | 6.43 | 60.2 |
| Tampon No. 6 | $6.86 \times 10^8$ | 8.83 | 1.01 | 94.0 |

[a] As determined by ELISA method (Reiser et al.)
[b] Log to the base 10.
All determinations were made after 24 hours at 37° C.
All data above are mean determinations of duplicate samples.

EXAMPLE 9

The mixture of glyceryl monolaurate and glyceryl dilaurate used in the experiments reported in Examples 1–7 hereof was obtained from Lauricidin, Inc. under the tradename of Lauricidin. As indicated earlier herein, this mixture was analyzed and found to contain 93% by weight of glyceryl monolaurate and 3.5% by weight of glyceryl dilaurate. Mixtures of glyceryl esters of lauric acid were obtained from two other sources. One such mixture was obtained Tampons comprising, respectively, 0.1%, 0.5% and 1.0% of Monomuls 90-L12 mixture based on the weight of the untreated test tampon.

Tampons treated with isopropyl alcohol without any ester therein were employed as controls. All samples were prepared and tested in duplicate according to the Tampon Sac Method described earlier herein. Test results are set forth in Table 9.

TABLE 9

IMPACT OF VARIOUS GLYCEROL MONOLAURATES ON GROWTH OF AND TSST-1 FORMATION BY *STAPHYLOCOCCUS AUREUS* (FRI-1169)

| SAMPLE | % ADD-ON | FINAL CONCENTRATION OF S. AUREUS CELLS (CFU/ml) | FINAL CONCENTRATION OF S. AUREUS CELLS[b] (/ml) | TOTAL AMOUNT TSST-1 PRODUCED[a] (ug) | REDUCTION IN TSST-1 FORMATION (%) |
|---|---|---|---|---|---|
| Control | 0.0 | $8.8 \times 10^7$ | 7.94 | 69.94 | — |
| Kessco | 0.1 | $1.28 \times 10^8$ | 8.10 | 45.24 | 35 |
| Glyceryl Monolaurate | 0.5 | $4.16 \times 10^7$ | 7.62 | 33.60 | 52 |
|  | 1.0 | $3.44 \times 10^7$ | 7.53 | 1.40 | 98 |
| Lauricidin* | 0.1 | $1.4 \times 10^7$ | 7.15 | 4.49 | 93 |
| Glyceryl Monolaurate | 0.5 | $1.3 \times 10^7$ | 7.11 | 3.93 | 94 |
|  | 1.0 | $3.2 \times 10^7$ | 7.50 | 0.39 | 99 |
| Monomuls | 0.1 | $1.28 \times 10^8$ | 8.10 | 2.41 | 96 |

TABLE 9-continued

IMPACT OF VARIOUS GLYCEROL MONOLAURATES
ON GROWTH OF AND TSST-1 FORMATION
BY *STAPHYLOCOCCUS AUREUS* (FRI-1169)

| SAMPLE | % ADD-ON | FINAL CONCENTRATION OF S. AUREUS CELLS (CFU/ml) | FINAL CONCENTRATION OF S. AUREUS CELLS[b] (/ml) | TOTAL AMOUNT TSST-1 PRODUCED[a] (ug) | REDUCTION IN TSST-1 FORMATION (%) |
|---|---|---|---|---|---|
| 90-L12 | 0.5 | $4.16 \times 10^7$ | 7.62 | 0.36 | 99 |
|  | 1.0 | $3.44 \times 10^7$ | 7.53 | 0.16 | 99 |

Kessco* contained 50% by weight of glyceryl monolaurate.
Lauricidin* contained 93% by weight of glyceryl monolaurate.
Monomuls 90-L12 contained 96% by weight of glyceryl monolaurate.
[a] As determined by ELISA method (Reiser et al.)
[b] Log to the base 10.
All determinations were made after 24 hours at 37° C.
All data above are mean determinations of duplicate samples.

It can be seen from the test data set forth in Table 9 that, for any given concentration (i.e. add-ons of 0.1%, 0.5% or 1.0% w/w) of ester mixture in the tampon, the final amount of TSST-1 produced under the described test conditions is inversely proportional to the concentration of glyceryl monolaurate in the ester mixture. Thus, for example, where the amount of ester mixture in the test tampons was held constant at the 0.5% add-on level, the final amounts of TSST-1 declined from 33.60 ug when the ester mixture contained 50% by weight of glyceryl monolaurate (i.e. Kessco*), to 3.93 ug when the ester mixture contained 93% by weight GML (i.e. Lauricidin*), to 0.36 ug where the ester mixture contained 96% glyceryl monolaurate (i.e. Monomuls* 90-L12). Similar reductions in the final amounts of TSST-1 produced were observed where the three ester mixtures were used at 0.1% and 1.0% by weight of the tampon. The results set forth in Table 9 suggest that glyceryl monolaurate (which contains two unreacted hydroxyl groups derived from glycerol) is more effective in inhibiting production of TSST-1 than glyceryl dilaurate (which contains a single unreacted hydroxyl group derived from glycerol).

EXAMPLE 10

In vivo Activity of Glyceryl Monolaurate-Impregnated Tampons

Test tampons were made as follows. Avtex rayon (100%) #SN2587 three denier was used as the test fiber. The fiber was scoured to remove Tween 20 and either left as unfinished or coated with glycerol monolaurate (Henkel Monomuls L-90)(hereinafter referred to as "GML"). The analytical determination of the monolaurate content of the material was 96.0%, 2.0% of the 1-3 diestar and 2.0% unidentified material. The fiber was coated as follows. Seventy-five pounds of rayon fiber was loaded into a holding tank and the tank filled with water (120 gallons total). Ammonia ($NH_3$) (29.4% v/v) was added to the water in the holding tank. The system was then heated to 200° F. for 30 minutes. The fiber was then washed with hot water (150° F.) three times, the wash water checked for any residual foam evidencing the presence of Tween 20. The fiber was then washed with cold water, 60° F.

The fiber was transferred to a centrifuge where it was spun while still hot for 5 minutes to remove excess water. The 75 lbs. of rayon initially contained 54 lbs. of water. The rayon was then opened by hand and placed back into the holding tank. Two restraining plates were placed over the fiber to reduce agitation and minimize foaming. Hot water (10°–200° F.) was added followed by four 5-pound samples of GML, each dissolved in five gallons of 170° F. water. The system was pressurized and heated to 190° F. and circulated for 30 minutes. After the system was allowed to drain, the fiber was taken to the centrifuge and spun for 5 minutes. At this point, there was 52 lbs. of water (70%) remaining. The temperature of the outside fiber was 160° F. while the temperature of the inside fibers was 175°–180° F.

The moist fiber was placed in a belt oven, which was heated to about 250°–260° F. This heat treatment further opened and dried the rayon fiber. The coated and unfinished fiber were then run through a Rando Webber followed by carding in order to form a workable ribbon from which to make tampons.

After the fiber was scoured or coated, dried and carded the rayon ribbon was used in the production of 2.30 g tampons. The fiber was compressed bidirectionally and held in a compression puck for five seconds. After compression, the tampons were placed into 0.62" o.d. applicators. The tampons were wrapped in cellophane and sealed. Control tampons were labelled (y) while GML-coated tampons were designated (x). The tampons were made as follows: Blanks were made by cutting the rayon into sections 2.75" in length by 3.0" in width. Fiber orientation for length was machine-direciton and for width, was cross-direction. The sections were either built up or torn down to obtain blank weights of 2.28 g. The rayon section was then hand-rolled and covered. For control blanks, the cover was 0.25 oz. Enka bicomponent fabric (2.75"×4.75"). For GML blanks, the cover was 0.25 oz. Enka bicomponent fabric coated with 2.4% GML solution. The cover was heat sealed to itself using a hand iron. A 8/5 White rayon string, available from Blue Mountain Industries, was cut to 13.0" lengths. The string was pierced through one end of each blank at a distance of ⅝" from the end on the piercing unit and then looped. Each blank was tested for anchor strength by manually pulling the strig after looping. The blanks were compressed bidirectionally (side-to-side, then end-to-end) and held in the compression puck for 5 seconds. Immediately after compression, the tampons were placed in Reggie three-piece applicator (0.62" o.d.). The pull string was not knotted. The tampons were wrapped in white cellophane sleeves and sealed.

The compressed tampons were analyzed for determination of the concentration of GML on the tampon fibers. The average concentration of GML on the tampons tested was 2.38% w/w.

The in vitro impact of the GML tampons compared to that of the unfinished tampons was evaluated using both the Holland Shake Flask Method and the Reiser Tampon Sac Methods for evaluation on TSST-1 formation by S. aureus. The Reiser Tampon Sac Method has been described above in Examples 1 and 7. The results of the determination of the impact of the GML (2.38% w/w) coated tampons is set forth in Tables 10 and 11. Table 10 shows that greater than 99.9% reductions in TSST-1 formation were noted when the tampons were evaluated using the following Holland Shake Flask Method: two liter triple-baffle flasks were autoclaved containing 500 ml of Difco Brain Heart Infusion Broth. After sterilization, five ml of a 24-hour old culture of S. aureus strain identified as 1187 was added to the flasks. Either 25.0-gram quantities of test material or no material (in the control flasks) were added to the flasks in duplicate. All flasks were incubated at 37 C with shaking at 160 rpm for 24 hours, at which time TSST-1 concentration and total S. aureus cell count determinations were made. TSST-1 level was determined using the ELISA test, while total cell counts were made using Standard Plate Count procedures.

Exposure of the GML and unfinished tampons to S. aureus using the Tampon Sac Method can be seen in Table 11. Reductions in TSST-1 formation ranging from 81.1% in media with blood to 95.9% without are demonstrated, while the impact on the total number of S. aureus cells was either none at all in the presence of blood or 9.1% in tubes without blood.

The Holland Shake Flask Method showed higher antimicrobial activity with the shaking and agitation of the system. This in vitro test method was not predictive of the in vivo situation. In contrast, the Tampon Sac Method was found to be the preferred in predicting the in vivo situation.

The in vivo evaluation of efficacy was performed as follows. Both control and GML tampons were mailed to the Southwest Research Institute in San Antonio, Tex., for evaluation for reduction to TSST-1 formation by S. aureus in the baboon vagina. Twelve female baboons were identified by immobilization with Ketamine HCl and vaginal examination for gross evidence of infection.

Unfinished control tampons had 5 ml of a S. aureus toxigenic strain grown in Brain Heart Infusion Broth for 24 hours at 37° C. absorbed onto their distal ends (ends distant from the string). Pre-weighed seed tampons were immediately introduced into the baboon vagina, without the use of a speculum, and the pull string cut. Rectal temperature and indirect systolic blood pressure was taken and recorded. Five milliliter blood samples were taken from the cephalic vein and the serum stored at −70° C. until analysis for the presence of anti-TSST-1 antibody and clinical chemistry could be executed.

Seed tampons were maintained intravaginally for twelve hours. After the first twelve hours, the baboon was immobilized with Ketamine HCl and the tampon was removed. The seed tampon was placed in a pre-weighed 4-oz. plastic cup. Tampon plus cup were weighed and the amount of tampon associated fluid was calculated. The tampon was transferred to a stomacher bag containing 50 ml of sterile saline (0.9% NaCl) and mixed for 60 seconds. The stomacher fluid was then submitted for quantitative determination of total S. aureus cell count and TSST-1 concentration. The total cell count determinations were made using standard plate count method and TSST-1 concentrations were determined using radioimmunoassay (R.I.A.).

All tampons inserted after the seed tampon were treated as previously described. After removal of the seed tampon, all baboons had control (y) tampons inserted intravaginally to allow for additional growth of S. aureus and TSST-1 production within the vaginal cavity. After twelve hours' additional incubation, the animals were divided in two sets of six whereby six baboons were tested with the control tampons and six with GML coated tampons. After the 48-hour exposure period, all animals had tampons inserted supplemented with 5.0 ml of their own blood serum because of diminished menstrual flow. Total viable S. aureus cell count and TSST-1 level determination were made on all tampons. After all tampons were processed and both toxin and cell count determinations were made, four animals were excluded from the study (two control animals and two GML test animals). In these animals, either the organism was not transferred to the vaginal cavity to initiate an infection, or less toxin or cell levels than those known to have been applied to the seed tampon were found. Table 12 sets forth the data of total toxin per milliliter of tampon associated fluid and total toxin on the tampons with the impact on cell count. Tha data shown is representative of four animals in each test group.

The data set forth in Table 12 demonstrate considerable decreases in toxin formation in the four animals wearing the GML tampons over those wearing the control tampons alone. FIGS. 1-4 represent the data of the impact of the GML tampons. Although initially the toxin level in the test animals wearing control tampons had higher TSST-1 levels, the GML tampons brought the level of toxin down significantly over that observed in the controls.

The data representing the total toxin produced per $10^6$ cells of S. aureus, thus normalizing the data with respect to individual cells, demonstrates the significant reduction in the tampons containing GML over the control tampons. A trend of increasing toxin in relation to bacterial cells was noted in the control animals after the addition of blood on the 60-hour tampons. The trend noted in the control animals appears to be a direct impact on the cells themselves and the growth curve. This trend was observed in the animals wearing the GML tampons.

The data set forth in Table 13 show a direct comparison of a percentage of the control of toxin on the tampon-associated fluid and total toxin formed in the tampons in comparison with the control tampons.

TABLE 10

IMPACT OF GML COATED TAMPONS ON TSST-1 FORMATION USING HOLLAND SHAKE FLASK METHOD

| SAMPLE | MEDIUM | TOTAL TSST-1 PRODUCED (ug) | REDUCTION (%) | FINAL CONC. OF VIABLE S. AUREUS CELLS (cfu/ml) | TOTAL AMOUNT OF VIABLE S. AUREUS CELLS (cfu) |
|---|---|---|---|---|---|
| S. aureus | BHI | 81.57 | — | $2.4 \times 10^9$ | $1.20 \times 10^{12}$ |
| Control Tampon | BHI | 1.62 | — | $1.92 \times 10^9$ | $9.60 \times 10^{11}$ |
| GML (2.38%) Tampon | BHI | <0.001 | 99.93 | <10 | $<5.00 \times 10^3$ |
| S. aureus | Blood* | 66.89 | — | $2.0 \times 10^9$ | $1.00 \times 10^{12}$ |
| Control Tampon | Blood | 6.23 | — | $2.40 \times 10^9$ | $1.20 \times 10^{12}$ |
| GML (2.38%) Tampon | Blood | 0.004 | 99.92 | $1.92 \times 10^4$ | $9.60 \times 10^6$ |

*Denotes defibrinated Sheep Blood added to BHI at 1.0% v/v concentration.

TABLE 11

IMPACT OF GML COATED TAMPONS ON TSST-1 FORMATION USING THE REISER TAMPON SAC METHOD

| SAMPLE | MEDIUM | TOTAL TSST-1 PRODUCED (ug) | REDUCTION (%) | CONC. OF VIABLE S. AUREUS CELLS (cfu/ml) | AMOUNT OF VIABLE S. AUREUS CELLS (cfu) |
|---|---|---|---|---|---|
| S. aureus | BHI[a] | 40.00 | — | $6.0 \times 10^8$ | $4.68 \times 10^9$ |
| Control Tampon | BHI | 65.06 | — | $6.0 \times 10^8$ | $4.68 \times 10^9$ |
| GML Tampon | BHI | 2.63 | 95.9 | $8.0 \times 10^7$ | $6.24 \times 10^8$ |
| S. aureus | Blood[b] | 54.27 | — | $8.4 \times 10^8$ | $6.55 \times 10^9$ |
| Control Tampon | Blood | 50.55 | — | $1.5 \times 10^7$ | $1.17 \times 10^8$ |
| GML Tampon | Blood | 9.52 | 81.1 | $3.6 \times 10^7$ | $2.80 \times 10^8$ |

[a]Denotes Brain Heart Infusion Agar.
[b]Denotes defribrineated Sheep Blood added to BHI at 1.0% v/v concentration.

EXAMPLE 11

In this Example 11, tampons comprising various fatty acid esters were tested to determine their effect on growth of and TSST-1 formation by S. aureus bacteria (FRI-1169). Test tampons of the kind used in Example 1 were used for this Example 11. Test tampons comprising 0.1%, 0.5%, 1.0% and 10% fatty acid ester based on the weight of the untreated test tampons were prepared according to the General Procedure described earlier herein and were tested according to the Tampon Sac Method described in Example 1. Duplicate test tampons without any fatty acid ester were used as controls. The test results are report in Table 14.

The following is a list of the fatty acid esters which were evaluated:
Tampon No. 1—2-Hydroxy-1-propyl laurate
Tampon No. 2—Diethylene glycol monolaurate The test results show that there was a marked reduction in the amount of TSST-1 produced by S. aureus strain FRI-1169 in the presence of the tampons treated with the various fatty acid esters when compared to the amount of TSST-1 produced in the presence of the untreated control tampons. The reduction in the amount of TSST-1 produced ranged from about 7% (in the case of 0.1% 2-hydroxy-1-propyl-laurate) to about 99% (in the case of 1.0% 2-hydroxy-1-propyl-laurate). No corresponding pattern of reduction in the number of viable S. aureus cells was observed.

EXAMPLE 12

Effect of Dodecyl Glycerol Ether on TSST-1 Toxin

In this Example, tampons containing dodecyl-glycerol-ether were tested to determine their effect on growth and TSST-1 formation of S. aureus bacteria (Strain FRI-1169). This ether derivative of glyceryl monolaurate was obtained from Henkel Corp. and identified as dodecyl glycerin ether with a OH⁻ value of 421, acid value of 0.4 and purity of 99%. The material was specified to be greater than 90% mono-dodecyl content.

Test tampons of the kind used in Example 1 were used for this Example 12.

Test tampons comprising 0.1, 0.5, and 1.0% fatty acid ether based on the weight of the untreated test tampons were prepared according to the General Procedure described earlier herein and were tested according to the Tampon Sac Method described in Example 1. Duplicate test tampons without any fatty acid ether were used as controls. The test results are reported in Table 14.

The test results show that the amount of TSST-1 produced by S. aureus bacteria in the presence of the tampons treated with 0.1%, 0.5%, and 1.0% w/w dodecyl-glycerol ether was reduced 96%, 99% and 99%, respectively, when compared to the amount of TSST-1 produced in the presence of a control tampon containing no dodecyl-glycerol ether. Whereas, at the end of the 24-hour incubation period, the total S. aureus cell concentration (expressed as log to the base 10) in the presence of the control tampon was 10.48, the total S. aureus cell concentration (expressed as log to the base 10) in the presence of tampons treated with 0.1%, 0.5%, and 1.0% w/w dodecyl-glycerol-ether was respectively, 8.07 (23% less), 6.72 (36% less), and 8.21 (22% less).

TABLE 14

Effect of Dodecyl-glycerol Ether on Growth and TSST-1 Formation By S. aureus

| Sample | Conc. of GML (%) | Final Conc. of S. aureus Cells (CFU/ml) | Final Conc. of S. aureus Cells[b] (/ml) | Total Amount TSST-1 Produced[a] (ug) |
|---|---|---|---|---|
| Control | 0 | $3.00 \times 10^{10}$ | 10.48 | 66.91 |
| Dodecyl glycerol ether | 0.1 | $1.17 \times 10^8$ | 8.07 | 2.77 |
| | 0.5 | $5.26 \times 10^6$ | 6.72 | 0.13 |
| | 1.0 | $1.65 \times 10^8$ | 8.21 | 0.06 |

[a]As determined by ELISA (Reiser et al.)
[b]Log to the base 10
All determinations were made after 24 hours at 37 C. All data above are mean determinations of duplicate samples.

EXAMPLE 13

A series of experiments were executed by Dr. M. E. Melish, Department of Pediatrics, University of Hawaii to determine the effect of glyceryl-monolaurate-treated cotton tampons on TSST-1 formation within a rabbit vagina and subcutaneous implantation.

Sexually mature female New Zealand White rabbits over 7 months of age weighing between 4 and 5.5 kg were utilized throughout the study. Simulated menses consisting of defibrinated rabbit blood mixed with 2.5 gm/dl (grams per deciliter) bovine serum albumin to yield a final protein concentration of 8.5 gm/dl, albumin concentration of 3.5 gm/dl and hemoglobin concentration of 9–11 gm/dl. Blood was taken from animals with no detectable anti-TSST-1 titer determined by radioimmuno binding assay. TSST-1 levels were measured in the plasma and tampon fluids by a liquid phase competitive binding RIA using radioiodianted TSST-1. This assay can detect TSST-1 concentrations above 0.6–1.3 ng/ml.

Vaginal Study

Tampons were prepared with 100% cotton fiber and ¼ oz bicomponent fusible fiber cover (Enka, made by the Enka Company). The cover was coated with 1.32±0.28% w/w glyceryl monolaurate while the control tampon consisted by 100% cotton fiber alone. The fibers, after carding, were rolled and enclosed in an Enka bag having the dimensions 1.2"×2.0". The fiber weight was 1.0 g with the string being 8's/5 rayon white.

Rabbits were anestheized with ketamine 35 mg/kg and xylazine 6 mg/kg. A tampon was inserted through the urogential sinus into the vagina above the urethra by means of a plastic applciator. Five ml of fluid ±1 cc of staphylococcal suspension (*S. aureus* strain FRI-1169) was applied to the tampon through the applicator. A string for tampon removal remained at the vulvar opening. Blood was obtained for baseline studies via the marginal ear vein. After 4 hours, the animal was again anesthetized, the tampon was removed by gentle traction upon the string, and a second tampon was inserted. Another 5.0 ml of sterile fluid without staphylococci was applied to the tampon and the second tampon was allowed to remain in place for 4.0 hours and then removed under anesthetic as before. A third tampon was inserted and another 5 ml of sterile fluid was injected. The tampons (test or glyceryl monolaurate-treated) were allowed to remain in the vagina for 14–16 hours to simulate overnight usage. Blood was obtained for TSST-1 quantitation, hematogic and clinical chemistry. Upon removal of the tampons, the weight was determined and the fluid was extracted. TSST-1 concentration, pH and cfu of staphylococci were measured by radioimmunoassay, pH meter, and plating of dilutions on mannitol salt agar. This model has been described in detial in Melisch, M. E. et al., "Vaginal tampon model for Toxic Shock Syndrome", Reviews of Infectious Dis. 11:5238–5247, 1989. The results of this example are presented in Table 15.

Results

The results presented in Table 15 show the effect of the control, untreated tampons as compared to glyceryl monolaurate treated tampons on TSST-1 formation. The data show that the glyceryl monolaurate treated tampons resulted in lower levels of TSST-1 formation tn the vaginas of rabbits when compared to the untreated control. Further, the effect of glyceryl monolaurate was most significant in the 16 hour exposure (Tampon #3).

Subcutaneous Study

Under ketamine and xylazine anestheisa, tampons (either treated with glyceryl monolaurate or untreated controls) were inserted into the loose subcutaneous tissue at the nape of the rabbits' neck. The tampon was then immediately moistened with saline and inoculated with live, washed staphylococci. Following microorganism injection, animals were monitored for fever, clinical changes, and had multiple blood sampling for BUN (blood urea nitrogen), creatinine, calcium and triglyceride laboratory determinations to determine whether the animals had become ill with TSS illness. Individual rabbits were considered to have TSS illness if their BUN or creatinine values exceeded 2 standard deviations and calcium values were below 2 standard deviations at 24 and/or 48 hours from uninfected control mean values. At such blood drawing, TSST-1 was quantitated using radioimmunoassay. TSST-1 was also measured in urine. The sample tampons (control or treated) were sampled repeatedly for TSST-1 content and cfu/ml staphylococci.

Results

The results of the evaluation of the effect of untreated (control) tampons as compared to glyceryl monolaurate-treated tampons in both TSST-1 formation and viable *S. aureus* FRI-1169 cells over days in the subcutaneous infection model are shown in Tables 16 and 17. In TAble 16, x represents the mean value measured, "range" represents the range of measurements and (N) represents the number of animals tested. Table 17 represents the number of animals that contracted TSS illness or died during the course of the experiment. The results clearly show in Table 17 that glyceryl monolaurate treated tampons resulted in lower TSST-1 formation. This effect on reduced TSST-1 and viable staphylococcus count was most pronounced in the 8-hour and 24-hour samples. These early values are more applicable to vaginal tampon use than subcutaneous infection. This reduction in TSST-1 formation translated to less TSS illness and reduced death for the rabbits implanted with glyceryl monolaurate treated tampons.

TABLE 15

Effect of Glyceryl Monolaurate Treated Tampons
On TSST-1 Production In Rabbit Vaginal Model

| Tampon Type | Tampons | | |
|---|---|---|---|
| | 1 TSST-1 (ng) | 2 TSST-1 (ng) | 3 TSST-1 (ng) |
| Cotton Control | 447 | 68 | 3448 |
| (Range) | (292–601) | (1–135) | (1915–4981) |
| Treated Cotton | 113 | 10 | 24 |
| (Range) | (64–162) | (5–14) | (2–47) |

TABLE 16

EFFECT OF GLYCERYL MONOLAURATE TREATED TAMPONS ON TSST-1
PRODUCTION AND CELL VIABILITY BY *S. aureus* (FRI-1169)
IN THE RABBIT SUBCUTANEOUS MODEL.
SUBCUTANEOUS TAMPON INFECTION
$7.5 \times 10^9$ CFU 1169
MEAN TSST-1 AND ORGANISM LEVELS IN TAMPON FLUIDS

| TAMPON TYPE | DAY 1 | | DAY 2 | | DAY 3 | | DAY 4 | |
|---|---|---|---|---|---|---|---|---|
| | TSST-1 NG/ML | CFU/ML | TSST-1 NG/ML | CFU/ML | TSST-1 NG/ML | CFU/ML | TSST-1 NG/ML | CFU/ML |
| NON GML COTTON | | | | | | | | |
| X | 134.4 | $1.3 \times 10^7$ | 463.6 | $3.6 \times 10^7$ | 357.2 | $1.2 \times 10^7$ | 522.0 | $4.6 \times 10^7$ |
| RANGE | 34.8–459.5 | | 43.1–3386.0 | | 45.8–2917.0 | | 33.8–2146.1 | |
| (N) | (13) | | (13) | | (11) | | (10) | |

TABLE 16-continued

EFFECT OF GLYCERYL MONOLAURATE TREATED TAMPONS ON TSST-1
PRODUCTION AND CELL VIABILITY BY S. aureus (FRI-1169)
IN THE RABBIT SUBCUTANEOUS MODEL.
SUBCUTANEOUS TAMPON INFECTION
$7.5 \times 10^9$ CFU 1169
MEAN TSST-1 AND ORGANISM LEVELS IN TAMPON FLUIDS

| TAMPON TYPE | DAY 1 | | DAY 2 | | DAY 3 | | DAY 4 | |
|---|---|---|---|---|---|---|---|---|
| | TSST-1 NG/ML | CFU/ML | TSST-1 NG/ML | CFU/ML | TSST-1 NG/ML | CFU/ML | TSST-1 NG/ML | CFU/ML |
| GML COTTON | | | | | | | | |
| X | 22.3 | $7.5 \times 10^6$ | 31.0 | $3.2 \times 10^6$ | 42.5 | $4.1 \times 10^6$ | 64.2 | $7.2 \times 10^7$ |
| RANGE | 0–81.9 | | 0–161.9 | | 0–358.4 | | 0–258.5 | |
| (N) | (13) | | (14) | | (14) | | (13) | |

TABLE 17

EFFECT OF GLYCERYL MONOLAURATE TREATED
TAMPONS IN THE RABBIT SUBCUTANEOUS MODEL
Subcutaneous Tampon Infection
$7.5 \times 10^9$ CFU FRI 1169

| | Control | | Treated | |
|---|---|---|---|---|
| Toxinemia | 1/15 | (6.7%) | 5/14 | (35.7%) |
| Toxin in Urine | 11/13 | (84.6%) | 12/13 | (92.3%) |
| TSS Illness | 13/15 | (86.7%) | 6/14 | (42.9%) |
| Death | 5/15 | (33.3%) | 2/14 | (14.3%) |

It has now been demonstrated that concentrations of glycerol monolaurate that do not have any observable effect on cell growth were still able to block TSST-1 production in S. aureus. It has also been demonstrated that GML inhibits Staphylococcal alpha hemolysin production. Dr. Richard Novick and Dr. Steven Projan have used the methods of gene fusion analysis and Northern and Western blotting techniques to demonstrate that, in the presence of GML, the structural gene for the TSST-1 toxin, the tst gene is not transcribed by the cells. Gene fusion analysis has also confirmed that transcription from the hla alpha hemolysin promoter is likewise inhibited by glycerol monolaurate.

Production of TSST-1 in *S. aureus* has been found to be dependent on several genetic and environmental factors. In order for a strain of *S. aureus* to express TSST-1 it must carry the tst gene encoding the structural gene for the protein. Approximately 20% of human clinical isolates have been found to carry the gene (Kreiswirth, B. N., P. M. Schlievert, and R. P. Novick, "Evaluation of coagulase-negative staphylococci for ability to produce toxic shock syndrome toxin-1", J. Clin. Microbiol. Vol. 25, p. 2028–2029, 1987). Another genetic component is the staphylococcal agr locus which is required for transcription of the tst gene (Kornblum, et al., "Molecular biology of the staphylococci", VCH Publishers, New York, p. 373–402, 1990).

TSST-1 production has also been reported to be responsive to a number of environmental factors. Production is manifest during post-exponential growth phase of cells in culture and apparently requires the presence of oxygen and a neutral Ph (Schlievert, et al., "Production of staphylococcal pyrogenic exotoxin type C: influence of physical and chemical factors", J. Infect. Disc., Vol 147, p. 236–242, 1983). Expression of TSST-1 may also be subject to catabolite repression. Control of TSST-1 production is therefore similar to that of a large number of other staphylococcal exoproteins such as alpha-hemolysin (Kornblum et al., 1990).

Because many of the reported cases of toxic shock syndrome involve tampon use, agents that block TSST-1 production and which can be incorporated into tampons without adversely affecting the vaginal flora have been sought. GML has been found to block TSST-1 production. It has also been reported that the surfactant Pluronic L-92 stimulated TSST-1 production (A. C. L. Wong. 1987. Factors Affecting Growth of *S. aureus* and Production of Toxic Shock Syndrome Toxin-1. Thesis for Doctor of Philosophy. pp 32–33). Experiments have now been performed that demonstrate that GML does specifically inhibit TSST-1 expression, as well as inhibiting alpha hemolysin production. These experiments also demonstrate that GML blocks TSST-1 and alpha hemolysin expression at the level of transcription.

SUMMARY OF NORTHERN AND WESTERN BLOT TESTS

Both the Northern and Western blot tests are used to detect biochemical species. The essential difference between a Northern and a Western blot is that a Northern blot is used for the detection of a species of RNA while the Western blot is used to detect specific proteins. Northern blots have been used in connection with the compositions and methods of this invention in order to detect the MRNA transcripts of the tst gene, the gene that encodes the TSST-1 protein. Western blots have been used to detect the TSST-1 protein itself.

The original blotting technology was developed to detect similar DNA species using DNA probes. The original blotting method was developed by Ed Southern and was called the "Southern blot".

Generally, DNA fragments were generated by restriction endonuclease digestions. These fragments were then separated by electrophoresis on an agarose gel, transferred to a nitrocellulose filter and then hybridized to specific DNA probes. The probes were usually labelled with a radioactive tracer in order to detect DNA fragments homologous to the probe. The tests use Xray film to find the radioactive tracer.

In a Northern blot, RNA is isolated from cells, although not necessarily purified, and the various species of RNA are separated electrophoretically on an agarose gel matrix that contains formaldehyde. The formaldehyde is intended to prevent RNA secondary structure from altering mobility. The RNA is separated by size, with the smaller species moving the most quickly through the gel matrix. The separated RNA molecules are transferred to a nitrocellulose filter and the RNA fixed to the gel by heating to 80 C in a vacuum. In the Northern blot technique used herein, the transfer is effected by capillary action using a high salt buffer solution. The RNA transcribed from a given gene is of a discreet size or sizes. Therefore, after hybridization with a gene-specific probe only one or a few radioactive bands are visible.

After transfer, the blot is hybridized to a probe specific for the gene being studied. Radiolabelled probes are preferable for use in this technique because of their ease of detection and quantitation. Probes can be prepared in a variety of ways, but most require a clone of the gene or gene segment being studied. The probe is hybridized to the blot using a nitrocellulose filter at a temperature optimal for RNA-DNA hydrogen bonding between complimentary bases: A-U; T-A; G-C; C-G (for DNA-RNA hybridization). The hybridization temperature can vary depending upon AT vs. GC content of the gene in question and the buffer conditions used. So wherever there is RNA on the filter that has a sequence capable of base pairing to the DNA probe the radioactive tracer will have hybridized. The signal is detected by using X-ray film which is placed over the blot.

Western blotting also involves electrophoresis however, in the case of Western blotting, the proteins are the macromolecules being analyzed and the detection method involves treatment of the filter with antibodies specific for the protein being analyzed. After the antibodies are bound, the filter is treated with a second antibody specific for the first and containing an enzyme that can be detected by a histochemical stain.

EXAMPLE 14

The mechanism by which glycerol monolaurate (hereinafter "GML") reduces TSST-1 toxin formation has been studied by R. Novick and S. Projan at the Public Health Research Institute in New York, N.Y. Their work showed that GML inhibits the formation of TSST-1 at the level of transcription in the cell. Northern blot analyses showed that TSST-1-specific MRNA production was inhibited in cultures where TSST-1 production was inhibited.

*S. aureus* strain Mn8 was isolated from a patient with menstrual-associated TSS. Mn8 is a high level producer of TSST-1. Strains FR1169 and FR1187, also TSST-1 producers were obtained from the University of Wisconsin, Food Research Institute. Strain RN7220, carrying pRN6735, is a producer of alpha hemolysin.

Brain Heart Infusion Broth (Difco) ("BHI") was used in all the experiments described. GML was prepared at 1% weight/volume (10 mg/ml) in 95% ethanol. Cultures used as inocula were grown at 37 C overnight without shaking in a 300 ml baffled, side arm, shaker flask (volume 10 ml)L followed by addition of 10 ml additional media. The flasks were then shaken at 240 revolutions per minute for one hour. This process has been found to produce a log phase culture. The culture was then subcultured by addition of 1 ml of culture into 20 ml total in a side arm, 300 ml shaker flask. Growth was monitored turbidometrically using a Klett-Sumerson photoelectric colorimeter with a green filter. Turbidostatic experiments were performed in a New Brunswick BioFlo fermentor (Model No. C30) by pumping in fresh medium containing BHI or BHI with GML at a replacement rate of greater than twice the log phase generation time, 100 minutes. This ensured the maintenance of a constant, post-exponential culture. GML was added at a concentration of 20 ug/ml at the time of subculturing. This time was termed t=0. To compensate for degradation of GML by enzymes, additional GML was provided at specific time intervals. The cultures were monitored and measured for growth of cells. The data show that *S. aureus* Strain Mn8 (both in the presence of GML and without GML within the growth media) grow equally well, showing no inhibition of growth by GML at the concentration employed. (See FIG. 1A).

A Western blot analysis was performed as follows: SDS-polyacrylamide gels were prepared and run according to the method of Laemmli (Laemmli, U. S., "Cleavage of structural proteins during the assembly of the head of bacteriophage T4", *Nature,* Vol. 227, p. 680–685), using a BioRad Mini Protean apparatus. Protein was transferred electrophoretically to nitrocellulose filter (Schliecher and Scheull BAS5) and detection of material reacting with the TSST-1 specific anti-serum was performed as described in Blake, et al., "A rapid, sensitive method of detection of alkaline phosphatase conjugated anti-antibody on Western blots", Anal. Biochem., Vol. 136, p. 175–179. Hyperimmune rabbit antiserum was raised against TSST-1. Anti-rabbit ICG antibody prepared in goat and conjugated to alkaline phosphatase was obtained from Sigma Chemical Co. (St. Louis, Mo.).

Western blot analysis showed that while there is no inhibition of growth, TSST-1 production is severely limited in the culture containing GML (See FIG. 2A). Similar results were also noted for two additional *S. aureus* strains 1169 and 1187. No extracellular TSST-1 could be detected in the culture.

Because no extracellular TSST-1 could be detected, the intracellular cell proteins were analyzed, as follows. The cells were harvested by centrifugation, washed, and lysed. When the celllysates were analyzed by Western blots, no material reacting to anti-TSST-1 antibody was detected in samples from the GML treated culture. This demonstrates the lack of TSST-1 within the cells.

A Northern blot analysis was performed in order to determine whether the GML was responsible for preventing the *S. aureus* cells from actually completing transcription of the structural gene for making TSST-1, the tst gene, as follows: Whole cell RNA extracts were prepared and separated on formaldehyde-agarose (1.25% weight/volume) gels and transferred to nitrocellulose according to the method of Kornblum et al. ("A rapid method to quantitate non-labeled RNA species in bacterial cells", Gene, Vol 63, p. 75–85, 1988) A probe specific for the tst transcript was prepared by nick translation (Rigby, P. W. J., M. Dieckmann, C. Rhodes and P. Berg (1975), "Labelling deoxyribonucleic acids in high specific activity in vitro by nick translation with DNA polymerase.", J. Mol Biol. 113:237–251. from a 287 bp HindII-BamHI fragment internal to the tst coding sequence (Blomster-Hautamaa et al., "The nucleotide and partial amino acid sequence of toxic-shock syndrome toxin-1", J. Biol Chem , Vol 261, p. 15783–15786; Kreiswirth, et al., "Evaluation of coagulase-negative staphylococci for ability to produce toxic shock syndrome toxin-1", J Clin. Microbiol Vol 25, p. 2028–2029).

Log phase *S. aureus* cells as previously described were centrifuged, resuspended, and lysed. The samples were separated by electrophoresis on a formaldehyde-agarose gel transferred to nitrocellulose and probed with nick-translated tst DNA. Although a strong tst-specific signal was seen in samples obtained from control cells, no signal was visible in the samples obtained from the GML-treated cells. Prolonged exposure of the Northern blot nitrocellulose filter showed no visible trace of tst-specific MRNA visible, indicating a profound inhibition of transcription of the TSST-1 MRNA. The results of this experiment showed that tst specific MRNA is produced only in the cells from the culture not treated with GML. The results of this Northern blot analysis are set forth in FIG. 2B.

Biochemical assays were performed as follows: Beta-lactamase activity was assayed spectrophotometrically at Ph 5.8 employing a chromogenic substrate, nitrocefin. Alpha hemolysin was assayed using an adaptation of the tube dilution method (Bernheimer, et al., "Isolation and composition of staphyslococcal alpha toxin", J. Gen. Microbiol., Vol. 30, p. 455–468). Three-fold serial dilution of culture supernatants were prepared in 10 Mm Tris 150 Mm NaCl Ph 7.3 and added to the substrate (0.5% whole, defibrinated rabbit blood). Samples were incubated at 37 C for 90 min. and then held at 4 C for 30 min. Hemolytic activity was measured by determining residual turbidity at 640 nm. 50% lysis points were determined by interpolation. Activities in hemolytic units are expressed as the reciprocal of the dilution yielding 50% lysis with Wood 46, a *Staphylococcus aureus* strain which produces only alpha hemolysin, used as a standard.

Figure 2A:
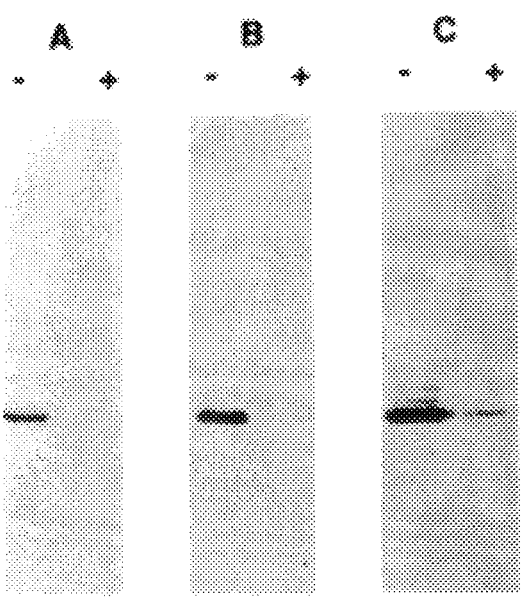
FIGS. 2A–C illustrate the results of Northern blot analysis of cell cultures.

Cultures of MN8, FRI1169 and FRI187 were grown as described above. GML was added at a concentration of 20 ug/ml at the time of subculturing, which is designated at t–0 in these experiments. To compensate for degradation of GML by lipases produced by *S. aureus*, additional GML was provided at the indicated time points. The results of a typical experiment are shown in FIGS. 1 and 2. FIG. 1 shows the growth curves of Mn8 cultures with and without GML. As can be seen, both cultures appear to grow equally well sharing no inhibition of growth by GML at the concentration employed. The Western blot shown in FIG. 2A depicts culture supernatants taken from the culture at the points indicated in FIG. 1. The Western blot clearly shows that, while there is no inhibition of growth, TSST-1 production is severely limited in the culture containing GML. Similar results were obtained for both FR1169 and FR1187, although both required more frequent GML supplementation to observe inhibition. If additional GML was not provided during the course of growth, TSST-1 production was delayed but not completely inhibited. Mn8 was also grown in a fermentor turbidostatically in a post-exponential phase of growth. TSST-1 production was inhibited only at concentrations of GML over 40 ug/ml as assayed by Western blot. When the medium was shifted from BHI and GML to BHI alone, TSST-1 production was fully restored after 100 minutes.

In addition to analyzing cell supernatants, the cells were harvested by centrifugation, washed and lysed. When the cell lysates were subsequently analyzed by Western blots, no material reacting with the anti-TSST-1 antibody was detected in samples from the GML-treated culture. However, a faint signal was seen in lysates of non-treated cells without GML. Thus, a faint signal represents the TSST-1 precursor, prior to secretion. The lack of even this precursor signal in the GML-treated cells indicates that the inhibition by GML is not at the level of secretion—otherwise one would have expected the accumulation of this precursor in the GML treated cells. It, therefore, follows that TSST-1 is not synthesized in GML-treated cells.

Figure 2B:
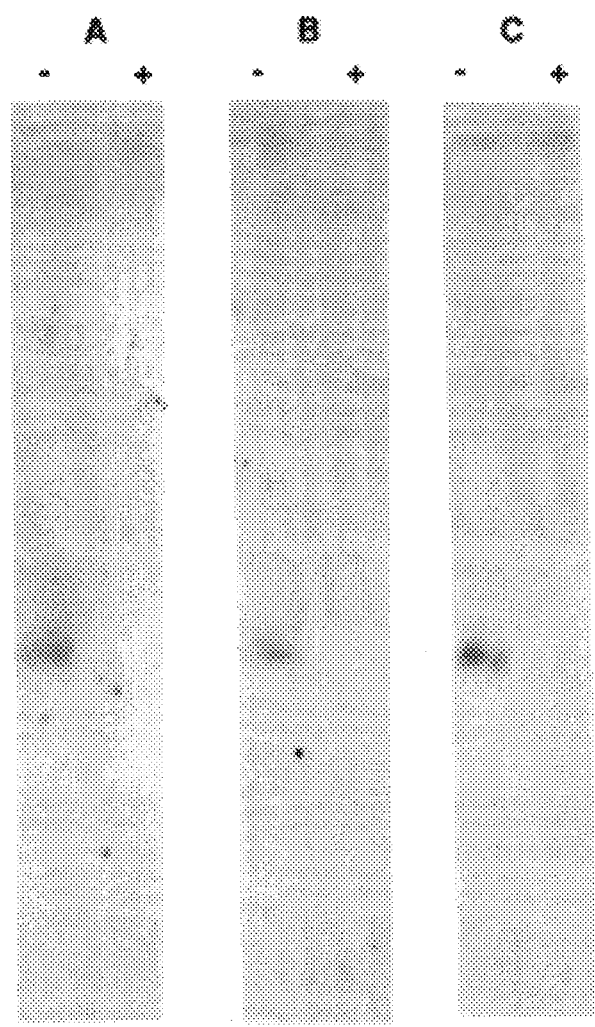
Figure 2C:
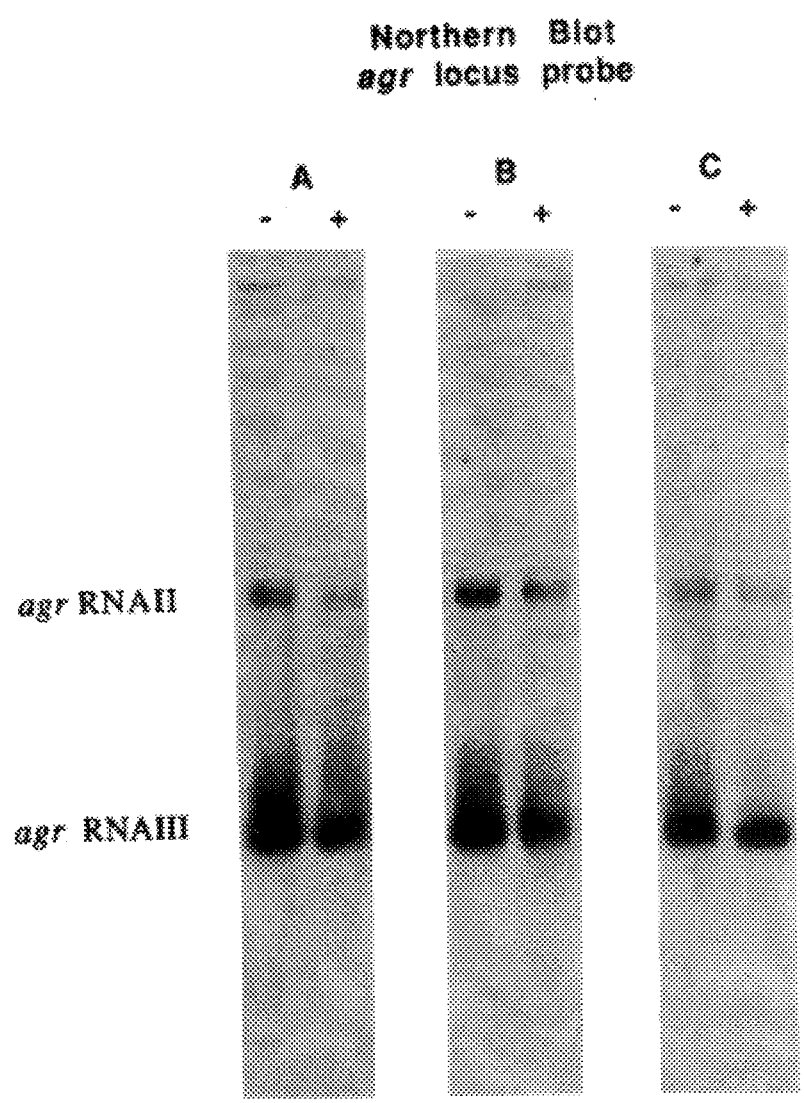
Figure 3A:
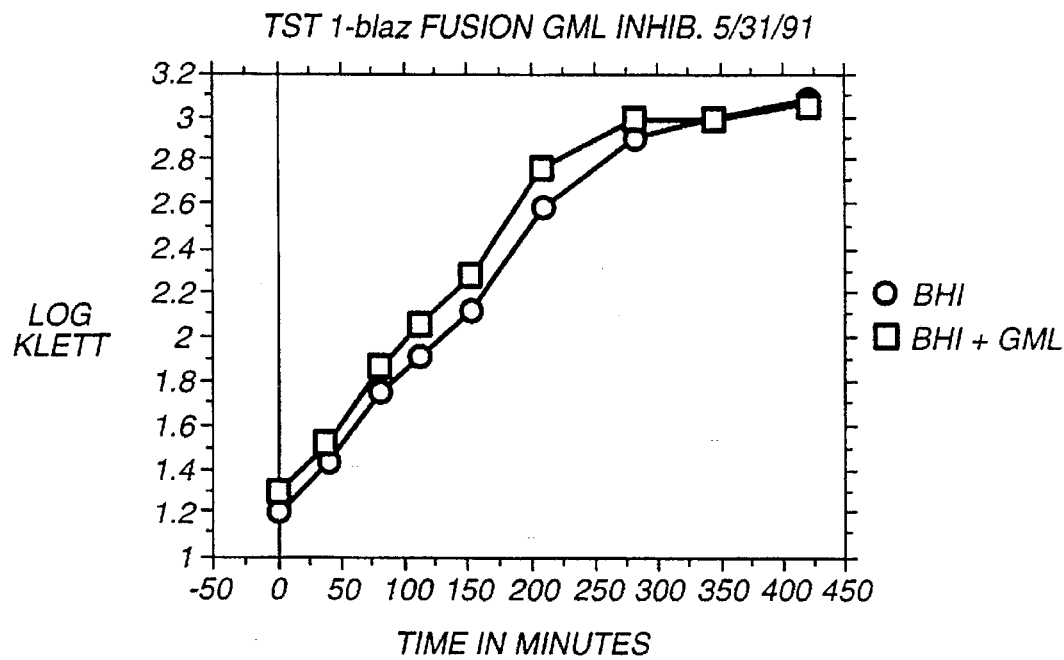
FIGS. 3A and 3B illustrate graphs of transcriptional fusion of TSST-1 promoter sequence to the structural gene encoding beta-lactamase activity.
Figure 3B:
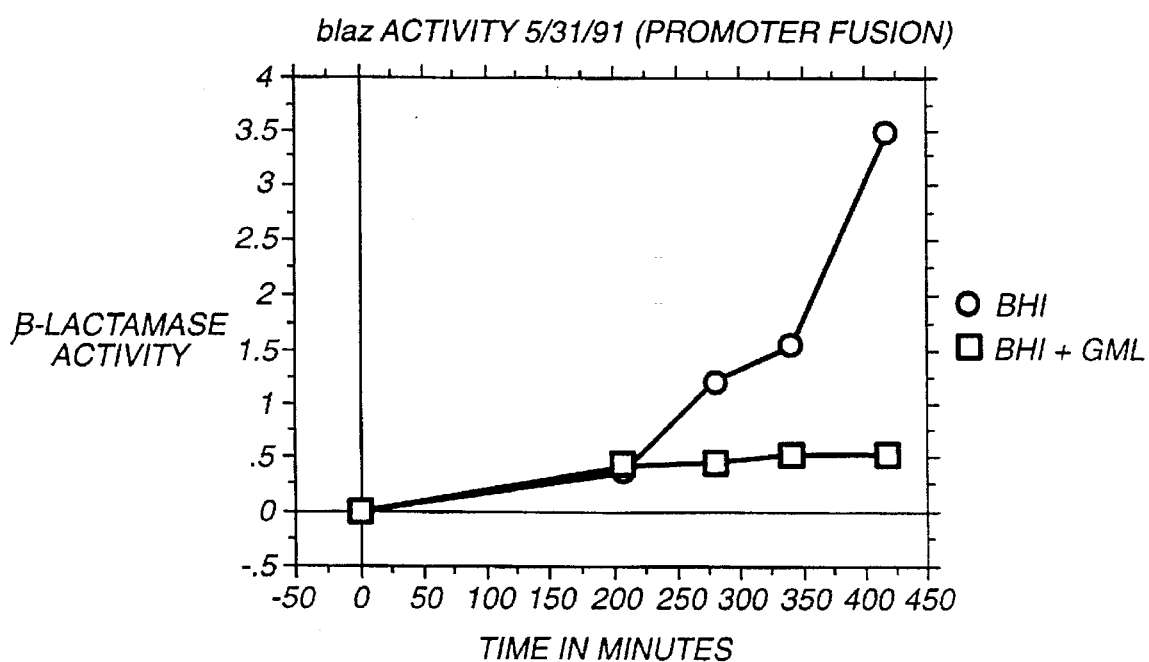
Figure 4A:
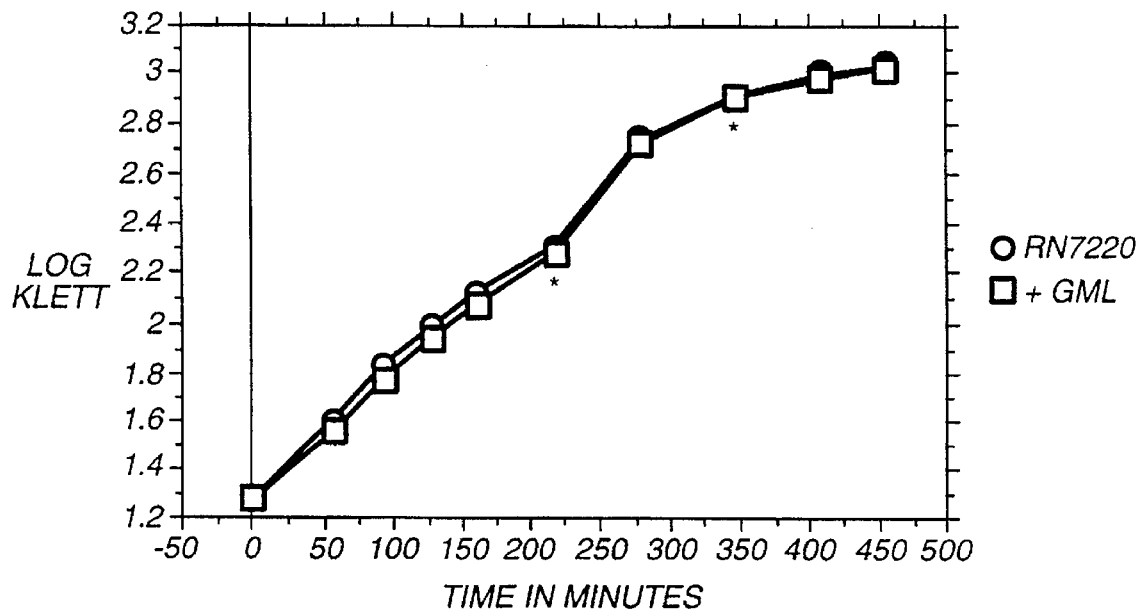
FIGS. 4A and 4B illustrate graphs showing inhibition of alpha hemolysin activity by one of the compounds of the present invention.
Figure 4B:
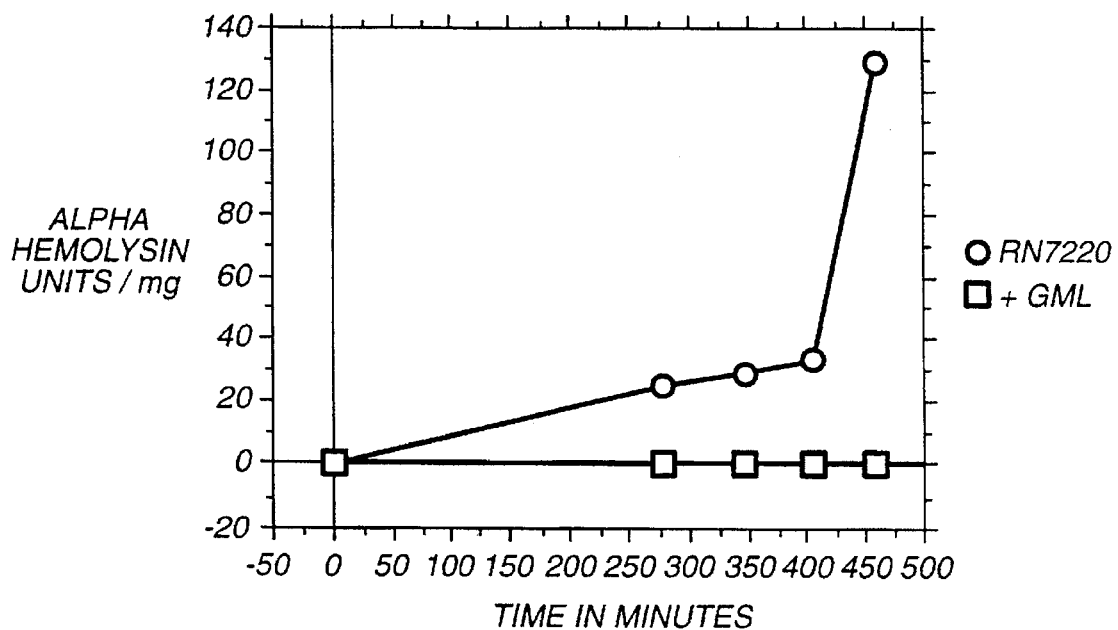

Transcription of the tst gene in GML-inhibited cultures was analyzed by Northern blot. Cell samples were obtained from the cultures shown in FIG. 1; whole cell RNA was prepared according to the quantitative method of Kornblum et al. as described above. These samples were separated by electrophoresis on a formaldehyde-agarose gel, transferred to nitrocellulose and probed with nick translated tst DNA. The results are shown in FIG. 2B. As can be seen from FIG. 2B, tst-specific MRNA is produced only in the cells from the culture not treated with GML, while no signal whatsoever is visible in the samples obtained from the GML treated cells. Prolonged exposure of the Northern blot nitrocellulose filter showed no trace of tst specific MRNA visible, thus indicating a profound inhibition of transcription of the TSST-1 MRNA. This result was confirmed using a transcriptional fusion of the TSST-1 promoter sequence to the structural gene encoding beta-lactamase. In these experiments, beta-lactamase activity is used as a reporter of transcription. Results of a typical experiment are shown in FIGS. 3A and 3B.

It has previously been shown that transcription of the tst gene was under the control of the *Staphylococcal* agr operon (accessory gene regulator). The agr locus controls the production of a large number of extracellular and cell wall bound proteins (e.g., alpha hemolysin and coagulase). Agr strains of *S. aureus*, both experimentally derived and naturally occurring, do not produce TSST-1 even when the tst gene is intact on the *S. aureus* chromosome (Kornblum et al. 1990). It was, therefore, thought possible that GML acts by inhibiting expression of the agr operon. This operon consists of two transcription units, RNAII and RNAIII). In the case of the agr system, it has been shown that the 600 nt transcript, RNAIII, is the positive effector for several agr-regulated genes, tst among them. However, Northern blot analysis of RNAII and RNAIII transcription, shown in FIG. 2C, revealed that the synthesis of agr transcripts is not inhibited by GML. Therefore, it is unlikely that GML inhibition of TSST-1 production involves inhibition of the Agr activation pathway.

Figure 5A:
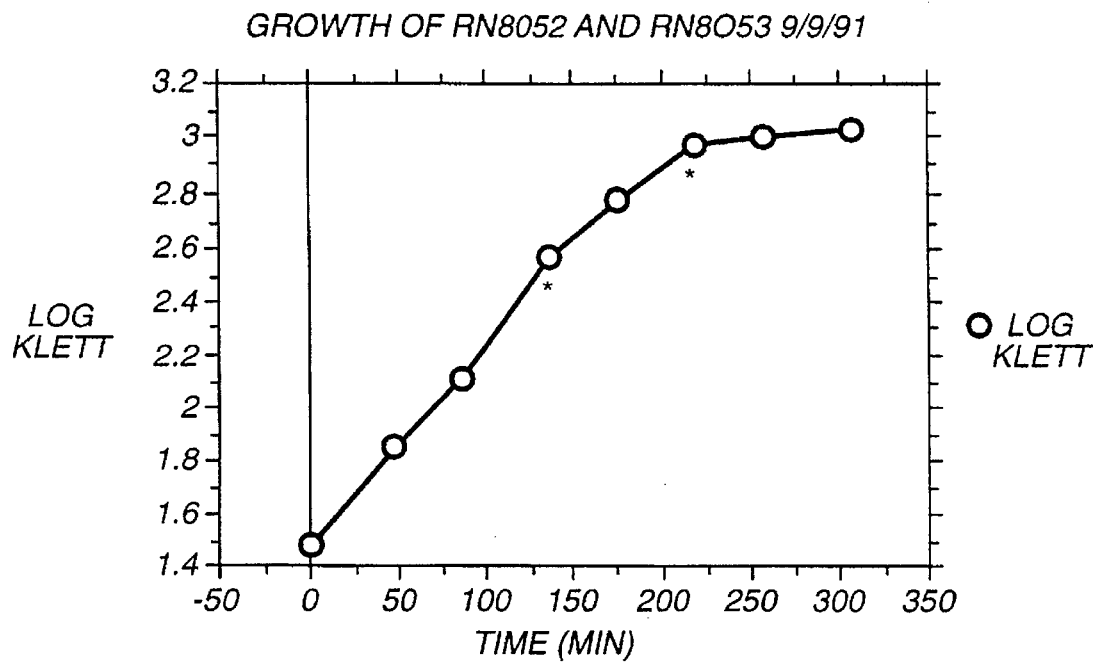
FIGS. 5A and 5B illustrate graphs confirming inhibition of alpha hemolysin activity by one of the compounds of the present invention using transcription analysis.
Figure 5B:
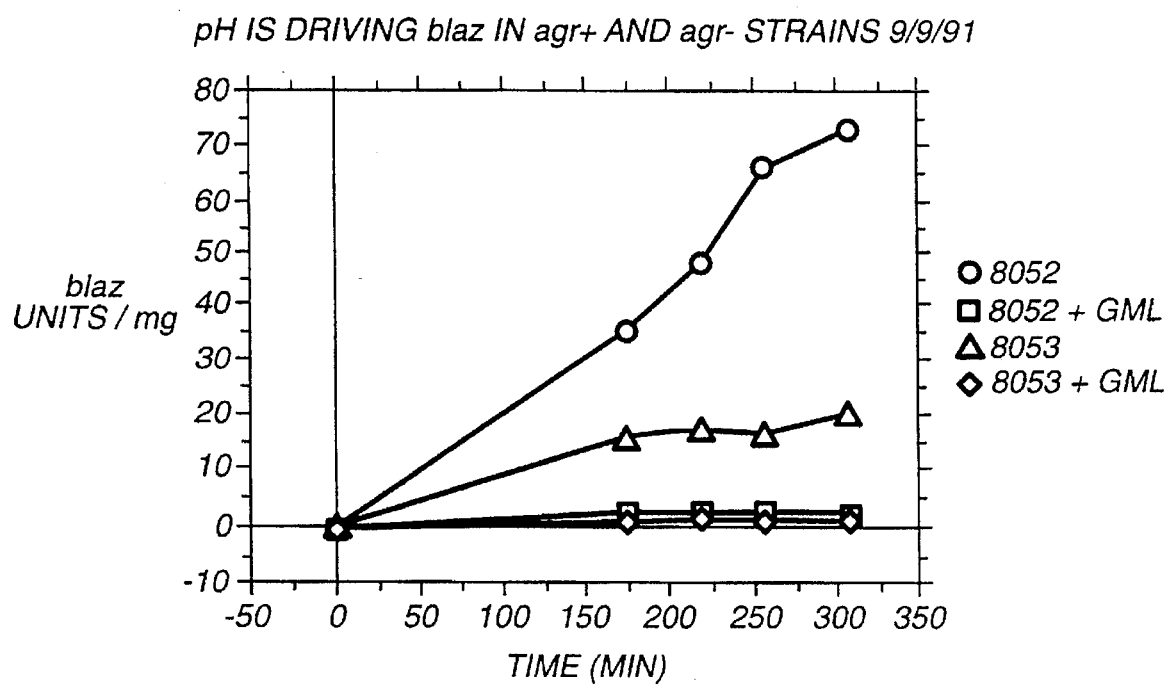

It has also been found that GML inhibits alpha hemolysin production. Strain RN7220 is a producer of alpha hemolysin. It produces neither beta-hemolysin nor delta-hemolysin. This strain has had the agr locus replaced with the tet(M) gene; the agr positive effector, RNAIII, is produced constitutively in this strain by virtue of a plasmid construct in which the blaz promoter is directing RNAIII transcription. This strain was grown in the same manner as the TSST-1 producers analyzed above. In these experiments, alpha hemolysin activity was assayed as described above with the results shown in FIG. 4A and 4B. As can be seen, as was the case with TSST-1, alpha hemolysin production was inhibited by GML even while cell growth remained unaffected. Using a similar gene fusion approach as described above, a fusion of the hla promoter to the beta-lacatamase reporter gene, it was shown that alpha hemolysin production was also inhibited at the level of transcription (FIGS. 5A and 5B).

Thus, these results show that the surfactant, GML, inhibits the production of alphahemolysin as well as TSST-1 by *S. aureus* at concentrations that do not affect growth. It was found that GML must be continuously supplied in order to observe inhibition of TSST-1 production. This is probably because the bacteria produce lipases capable of degrading lipids such as GML. Production of both of these extracellular virulence factors was further shown to be inhibited at the level of transcription by a mechanism that remains to be elucidated. Possibly, the target of GML inhibition may be signal transduction pathways that regulate expression of exoproteins.

Production of exoproteins by *S. aureus*, including both TSST-1 and alpha-hemolysin, require a functioning agr locus. However, it has been demonstrated here that expression of the agr transcripts is not affected by GML. The fact that agr is apparently not directly involved in the GML effect may indicate that other signal transduction systems are involved in TSST-1 and alpha-hemolysin expression. It has recently been shown that in addition to agr, a separate, temporal signal is required for alpha hemolysin expression in *S. aureus* (Vandenesch, et al., "A temporal signal, independent of agr, is required for hla but not spa transcription in *Staphylococcus aureus*", J. Bacteriol., Vol. 173, p. 6313–6320). It is therefore possible that GML acts by interfering with the transduction of this temporal signal.

The practical significance of these findings, therefore, is that absorbent products such as tampons, wound dressings or nasal packing material and the like, which are capable of acting as reservoirs for the continuous supply of GML and related compounds, can block the production of toxins by pathogenic Staphylococci without significantly affecting the flora normally found in the vaginal cavity, on skin or in the nasal cavity.

What is claimed is:

1. A method of inhibiting the production of TSST-1 toxin in mammals comprising exposing TSST-1 toxin-producing *Staphylococcus aureus* bacteria to an absorbent product comprising a compound selected from the group consisting of:

a) monoesters of a polyhydric aliphatic alcohol and a fatty acid containing from eight to eighteen carbon atoms and wherein said monoester has at least one hydroxyl group associated with its aliphatic alcohol residue;

b) diesters of a polyhydric aliphatic alcohol and a fatty acid containing from eight to eighteen carbon atoms and wherein said diester has at least one hydroxyl group associated with its aliphatic alcohol residue; and c) mixtures of said monoesters and diesters, said compound being present in an amount which is effective to inhibit the production of toxic shock syndrome toxin-1 by *Staphylococcus aureus* bacteria when said product is exposed to said bacteria.

2. A method according to claim 1 wherein said absorbent is a catemenial tampon.

3. A method according to claim 2 wherein said tampon is applied to a menstruating mammal.

4. A method according to claim 3 wherein said tampon is applied to a menstruating mammal in its vagina.

5. A method according to claim 1 wherein said fatty acid is lauric acid.

6. A method according to claim 1 wherein said polyhydric alcohol is glycerol.

7. A method according to claim 1 wherein said compound is glyceryl monolaurate.

8. A method according to claim 1 wherein said absorbent product is inserted subcutaneously in said mammal.

* * * * *